(12) United States Patent
Enk et al.

(10) Patent No.: US 11,642,480 B2
(45) Date of Patent: May 9, 2023

(54) DEVICES AND METHODS FOR VENTILATING A PATIENT

(71) Applicant: Ventinova Technologies B.V., Eindhoven (NL)

(72) Inventors: Dietmar Enk, Coesfeld (DE); Thomas Heinrich Barnes, Warlingham Surrey (GB); Dirk Theodorus Andreas van Asseldonk, Veghel (NL)

(73) Assignee: Ventinova Technologies B.V., Eindhoven (NL)

( * ) Notice: Subject to any disclaimer, the term of this patent is extended or adjusted under 35 U.S.C. 154(b) by 461 days.

(21) Appl. No.: 16/481,173

(22) PCT Filed: Jan. 25, 2018

(86) PCT No.: PCT/EP2018/051808
§ 371 (c)(1),
(2) Date: Jul. 26, 2019

(87) PCT Pub. No.: WO2018/138191
PCT Pub. Date: Aug. 2, 2018

(65) Prior Publication Data
US 2019/0388634 A1 Dec. 26, 2019

(30) Foreign Application Priority Data
Jan. 27, 2017 (DE) .......... 102017101645.7

(51) Int. Cl.
*A61M 16/00* (2006.01)
*G16H 20/40* (2018.01)
*G16H 40/63* (2018.01)

(52) U.S. Cl.
CPC ...... *A61M 16/024* (2017.08); *A61M 16/0051* (2013.01); *A61M 16/026* (2017.08); *G16H 20/40* (2018.01); *G16H 40/63* (2018.01); *A61M 2016/0027* (2013.01); *A61M 2205/3334* (2013.01); *A61M 2205/502* (2013.01); *A61M 2205/583* (2013.01); *A61M 2230/46* (2013.01)

(58) Field of Classification Search
CPC ............ A61M 15/024; A61M 16/0051; A61M 16/026; A61M 2205/3334; A61M 2230/46
See application file for complete search history.

(56) References Cited

U.S. PATENT DOCUMENTS

| 5,915,381 A * | 6/1999 | Nord .................... A61M 16/024 128/204.26 |
| 6,390,091 B1 | 5/2002 | Banner et al. |
| 2006/0000475 A1 | 1/2006 | Matthews et al. |
| 2006/0086357 A1 | 4/2006 | Soliman et al. |
| 2007/0157930 A1 | 7/2007 | Soliman et al. |

(Continued)

FOREIGN PATENT DOCUMENTS

| DE | 69918279 T2 | 7/2005 |
| EP | 0215433 | 3/1987 |

(Continued)

*Primary Examiner* — Margaret M Luarca
(74) *Attorney, Agent, or Firm* — Occhiuti & Rohlicek LLP (57) ABSTRACT

The present invention relates to a plurality of ventilation devices, to ventilation devices having visualization apparatuses, and to methods for operating the ventilation devices. The intent is to minimize the energy input into the at least one airway of a patient as a result of the ventilation.

14 Claims, 4 Drawing Sheets

(56) References Cited

U.S. PATENT DOCUMENTS

2007/0272242 A1 11/2007 Sanborn et al.
2008/0294060 A1 11/2008 Haro et al.
2014/0048072 A1 2/2014 Angelico et al.

FOREIGN PATENT DOCUMENTS

| EP | 1295620 | 3/2003 |
| WO | WO2008/113752 | 9/2008 |
| WO | WO2015/004229 | 1/2015 |

* cited by examiner

DEVICES AND METHODS FOR VENTILATING A PATIENT

CROSS REFERENCE TO RELATED APPLICATIONS

This application is a National Phase under 35 USC 371 of International Application No. PCT/EP2018/051808 filed on Jan. 25, 2018, which claims priority to German Application No. 10 2017 101 645.7 filed Jan. 27, 2017, the contents of which are hereby incorporated by reference in their entireties.

The subject matter of the present invention relates to a ventilation device, a ventilation device having a visualization apparatus, and a method for ventilating a patient. The ventilation device comprises at least a fluid supply unit and additionally a fluid discharge unit that are suitable for respectively supplying a fluid (in particular at least primarily respiratory gas) into at least one airway, i.e., into a lung part or into the lung, of a patient and for discharging the fluid from this airway.

When a patient is ventilated, a mask or a tube is normally used via which a gas or gas mixture, in particular oxygen and air, is supplied at low pressure to the airway sealed off from the outside. Alternatively, however, such a gas or gas mixture may also be injected in pulses at a high pressure and high flow rate through a thin lumen (a catheter, cannula, or tube) into the airway that is open to the outside (so-called jet ventilation). This method is currently used in particular in diagnostic and therapeutic procedures in the region of the upper airway (endotracheal or transtracheal jet ventilation). This method can also be applied in emergency situations outside the hospital environment or in inpatient situations within hospitals.

In transtracheal jet ventilation, a patient may be supplied with oxygen or a fluid by a catheter that is introduced directly into the trachea through the skin, or a cannula thus placed. These methods (transtracheal/endotracheal) are an integral part of the currently valid algorithms for managing difficult airways and, in particular, the situation in which a patient cannot be ventilated or intubated by conventional means (so-called "cannot ventilate, cannot intubate" situation).

Furthermore, gas flow reversing devices with which ventilation (inhalation and exhalation) can also take place exclusively via a lumen are known from WO 2008/113752 A1 and WO 2015/004229 A1.

Artificial or mechanical ventilation takes place either in a controlled manner or in the form of assisted spontaneous respiration. In the first case, the ventilation device (respirator) has complete control over the breathing pattern, whereas in the second case the at least partially spontaneously breathing patient has considerable influence over the breathing pattern. However, a common feature of all forms of ventilation is that the ventilation device almost exclusively influences the inhalation phase. From the perspective of the respirator, the exhalation can take place passively; i.e. the energy stored in the elastic tissue elements of the lung and thorax drives the exhalation.

Various ventilation methods are known. Volume-controlled ventilation is usually carried out, in which all the ventilation parameters are predefined. The target parameter and control parameter is the tidal volume (breathing volume) $V_T$. The resulting airway pressures are dependent on the volumes that are set and on the conditions of the patient's pulmonary system. Adjustment parameters are therefore volumetric flow, ventilation frequency, peak inspiratory pressure (PIP) and end-expiratory pressure (EEP), which include positive end-expiratory pressure (PEEP), zero end-expiratory pressure (ZEEP), and negative end-expiratory pressure (NEEP). The following discussion always refers to PEEP. The peak inspiratory pressure (PIP) denotes the highest positive pressure that is generated artificially in the airway during ventilation. It may also be provided as an alarm limit so that an exceedance of this pressure value is preferably prevented at all times. The positive end-expiratory pressure (PEEP) denotes a positive pressure that is generated artificially in the airway during ventilation and that is present after completion of the exhalation.

In pressure-controlled ventilation, an initially high volumetric flow is continuously reduced when a pressure rise in the airway or outside the airway, in the ventilation device, for example, is detected. The target parameter and control variable is therefore the pressure. An adjustment of the volumetric flow is thus not possible here; however, the volumetric flow is detected, and alarm limits may be defined.

In contrast to the spontaneous respiration of a patient, in artificial ventilation the fluid is supplied counter to the elasticity of the airway. Due to the increased pressure in the thorax, PEEP and PIP reduce the return flow of the venous blood to the heart, as a result of which the cardiac output may drop. Conversely, congestion occurs in the superior and inferior vena cava, with corresponding pressure increases in the upstream organs. Depending on the level of the PEEP and PIP, this may result in damage and functional impairment of the brain, liver, kidneys, and other organs.

On this basis, the object of the present invention is to propose an improved ventilation device and an improved ventilation method. In particular, the ventilation is intended to take place in a manner that is tailored to the individual to the greatest extent possible; i.e. the characteristics of the patient to be ventilated are to be taken fully into consideration. Furthermore, the ventilation should be as gentle as possible, and damage to the airways and other organs must be prevented in every case. In particular, a ventilation device is proposed which allows such ventilation to be carried out.

This object is achieved by ventilation devices having the features of claim 1 and also by methods having the features of claim 9. Advantageous variants and embodiments of the ventilation devices and of the methods are the subject matter of the respective dependent claims. It is noted that the features specified individually in the dependent claims can be combined with one another in a technologically meaningful way and define further embodiments of the invention. Furthermore, the features specified in the claims are rendered more precisely and explained in more detail in the description, with further preferred embodiments of the invention being presented.

A (first) ventilation device for ventilating a patient is proposed, comprising at least a fluid supply unit and a fluid discharge unit that are suitable for respectively supplying a fluid into at least one airway, i.e., into a lung part or into the lung, of a patient and for discharging the fluid from this airway; and further comprising a control device. The control device, at least during a ventilation process for the at least one airway, i.e., during the at least one-time supply of the fluid into the at least one airway and the at least one-time discharge of the fluid from the at least one airway by operating the ventilation device, is configured for setting a profile of a pressure P [cm H$_2$O or millibar] in the airway, and a profile of a volume V [milliliter] of the fluid supplied to the airway and discharged from the airway according to $V=f_{ZP}(P)$ and $V=f_{AP}(P)$, or according to $P=f_{ZV}(V)$ and $P=f_{AV}(V)$, wherein the ventilation process takes place within a pressure interval; wherein the ventilation process is settable by the control device in such a way that a) over at least 60%, in particular at least 80%, of the pressure interval, a ratio of an absolute value of a measure of the change in the first volume that is present at a pressure $P_0$ while supplying the fluid, i.e., $df_{AP}/d(P)(P_0)$ and an absolute value of a measure of the change in a second volume that is present at the same pressure $P_0$ while discharging the fluid, i.e., $df_{ZP}/d(P)(P_0)$ or b) over at least 60%, in particular at least 80%, of the volume interval, a ratio of an absolute value of a measure of the change in the first pressure that is present at a volume $V_0$ while supplying the fluid, i.e., $df_{AV}/d(V)(V_0)$ and an absolute value of a measure of the change in a second pressure that is present at the same volume $V_0$ while discharging the fluid, i.e., $df_{ZV}/d(V)(V_0)$, has a value of at least 0.5 and at most 2.0.

In particular, the volume [milliliter] is determined via the control device. A supply rate or a discharge rate of the fluid (i.e., a volumetric flow rate in milliliters per unit time) is hereby measured or monitored. In particular, the pressure [cm $H_2O$ or millibar] that is present in the airway is monitored via a pressure sensor, and the control device processes this value of the pressure.

The measure of the change in the first volume that is present at a pressure $P_0$ is, for example, the slope of a volume-pressure curve in a volume-pressure diagram. The pressure is plotted along one axis and the volume is plotted along the other axis. The curve has a first curve section $V=f_{ZP}(P)$ or $P=f_{ZV}(V)$, and a second curve section $V=f_{AP}(P)$ or $P=f_{AV}(V)$, wherein the first curve section represents the profile of the supplied volume V and of the pressure P while supplying the fluid into the at least one airway, and the second curve section represents the profile of the discharged volume V and of the pressure P while discharging the fluid from the at least one airway. The slope is determined by the first derivative of the respective function $V=f_{ZP}(P)$ (or $P=f_{ZV}(V)$) and $V=f_{AP}(P)$ (or $P=f_{AV}(V)$), i.e., $df_{AP}/d(P)(P_0)$ and $df_{ZP}/d(P)(P_0)$. Thus, the control device sets the ventilation process in such a way that over at least 60%, in particular at least 80%, of the pressure interval, a ratio of an absolute value of a first slope of the first curve section at a pressure $P_0$, i.e., $df_{ZP}/d(P)(P_0)$, and an absolute value of a second slope of the second curve section, i.e., $df_{AP}/d(P)(P_0)$, at the same pressure $P_0$, has a value of at least 0.5 and at most 2.0. The value of the result of the equation $[df_{AP}/d(P)(P_0)]/[df_{ZP}/d(P)(P_0)]$ should thus be at least 0.5 and at most 2.0. In particular, P0 is thus any pressure within the pressure interval or within a 60% or 80% portion of the pressure interval. The above statements similarly apply for the profiles of the functions $P=f_{ZV}(V)$ and $P=f_{AV}(V)$.

The absolute value indicates the value of the result, i.e., the measure of the change and of the slope, regardless of its algebraic sign.

In particular, it is proposed that the control device is configured for determining a profile of the pressure P in the airway and of a profile of a volume V of the fluid that is supplied to the airway and discharged from the airway for compliance of the patient according to one of $V=f_{CP}(P)$ or $P=f_{CV}(V)$, wherein the ventilation process is settable in such a way that a) over at least 60%, in particular at least 80%, of the pressure interval, a ratio of each of $df_{AP}/d(P)(P_0)$, $df_{ZP}/d(P)(P_0)$ and an absolute value of a measure of the change in the first volume of the compliance that is present at a pressure $P_0$, i.e., $df_{CP}/d(P)(P_0)$, or b) over at least 60%, in particular at least 80%, of the volume interval, a ratio of each of $df_{AV}/d(V)(V_0)$, $df_{ZV}/d(V)(V_0)$ and an absolute value of a measure of the change in the first pressure of the compliance that is present at a volume $V_0$, i.e., $df_{CV}/d(V)(V_0)$, has a value of at least 0.5 and at most 2.0.

In particular, the ventilation process is settable in such a way that over at least 60%, in particular at least 80%, of the pressure interval or of the volume interval, the ratio has a value of at least 0.67 and at most 1.5.

The ventilation process is preferably settable in such a way that over at least 60%, in particular at least 80%, of the pressure interval or of the volume interval, the ratio is greater or lesser than 1.0, in particular greater than 1.1 or less than 0.9.

The ventilation process, in particular at the start of the supplying of the fluid and at the start of the discharging of the fluid, and at the end of the supplying and at the end of the discharging, is set in such a way that the stated ratios are present here (for example, starting from these points, over 30% or over 40% of the pressure interval or of the volume interval in each case, so that these ratios are present over a total of 60% or 80% of the pressure interval or of the volume interval).

The underlying concept of the invention is to carry out ventilation of the patient with the lowest possible energy input, i.e., low absorption of energy by the airway (also referred to below as energy loss E). A low energy input into the airways of the patient also means the least possible damage to the airways and other organs of the patient.

Such minimization of the energy input (the energy loss E) is achieved in particular by completely controlling and monitoring the ventilation process with regard to the supply and discharge of fluid in and out of the at least one airway. Thus, in particular the fluid supply rate and the fluid discharge rate are determined, monitored, and controlled by the control device, in particular at any point in time.

This control and monitoring of the ventilation process (i.e., the supply and discharge of fluid in and out of the airway) takes place in particular along a compliance curve of the airway of a patient, which may be represented in a volume-pressure diagram. This compliance curve depicts a (minimum) pressure interval, optionally starting from a predefined PEEP or PIP, in which a predefined volume of the fluid is supplied and discharged. The ventilation of the patient should now take place during the supply and during the discharge of the fluid in such a way that a volume-pressure curve of the particular ventilation process is as close as possible to the compliance curve. However, it is has been found that other factors should also be taken into account for minimizing the energy input. However, these may be combined individually or, of course, (just) in combination with the respective other factors.

For the devices and methods proposed here, in particular at least one, optionally multiple or even all, of the following parameters (for example, based on empirical values, patient data, compliance of the airway, resistance of the at least one airway (ascertainable by plethysmography, for example), etc.) or values of the parameters is/are proposed or predefined for the operator of the devices or by the method, in which the ventilation of the patient is to take place: PEEP [centimeters water column—cm $H_2O$, or millibar], PIP

[centimeters water column—cm H$_2$O, or millibar], volumetric flow rate [milliliters/minute], ratio of the duration of supplying the fluid to the duration of discharging the fluid from the airway—i.e., I/E (duration of inhalation/duration of exhalation).

In particular an I/E ratio of 1:1 is proposed, wherein deviations of up to 20% in particular are possible, and wherein the exhalation may also last longer, in particular up to a ratio of 1:1.5. A further deviation is made in particular only when this ratio is not applicable to the patient (for example, due to disease, abnormality, etc.).

It has been found in particular that the first slope of a first curve section of a volume-pressure curve, representable in a volume-pressure diagram, and the second slope of a second curve section, at the same pressure $P_0$ in each case (the pressure $P_0$ lies within the pressure interval), should have approximately the same value in a largest possible range of the pressure interval. The same applies for a volume $V_0$, wherein the first slope of a first curve section of a volume-pressure curve, representable in a volume-pressure diagram, and the second slope of a second curve section, at the same volume $V_0$ in each case (the volume $V_0$ lies within the volume interval), should have approximately the same value in a largest possible range of the volume interval.

The control device on the one hand controls and monitors the pressure and volume profiles while fluid is supplied into the at least one airway. On the other hand, the discharge of the fluid from the airway is now controlled and monitored as a function of the profile of this first curve section. In particular, no passive exhalation, which typically would produce a second curve section that differed greatly from the first curve section, is allowed here. In contrast, it is proposed to also actively monitor and control the discharge of the fluid by the control device, wherein the second curve section approximates the profile of the first curve section.

Initial tests with these types of ventilation devices and methods have shown that damage to the at least one airway (ventilator-induced lung injury (VILI)) may be at least reduced or even effectively prevented by such control of the ventilation.

In particular it is proposed, during ventilation of the at least one airway of the patient, to determine the compliance C of the airway, and to carry out the ventilation taking the determined compliance into account. The determination or the additional estimation of a profile of at least one subregion of a compliance curve takes place by supplying and/or discharging the fluid to/from the at least one airway and by determining at least one value of the compliance. The following applies for the compliance C: C=delta V/delta P [milliliter/millibar or milliliter/cm H$_2$O].

The compliance indicates how much fluid, i.e., a volume delta V [milliliter], is introduced into the at least one airway or is removed from the airway, so that a pressure in the airway changes by a pressure difference delta P [millibar]. The control device, taking into account the determined or additionally estimated profile of the at least one subregion of the compliance curve, determines a position of a pressure interval with the pressures P1 and P2, and sets these pressures on the ventilation device (for example, PEEP as P1 and PIP as P2) in such a way that at least one ventilation process, i.e., an inhalation and/or an exhalation, takes place between these pressures P1 and P2 and an absolute value of the compliance of this ventilation process is as large as possible.

A minimization of the energy input is achieved by determining the lowest possible pressure at which a required breathing volume $V_T$ (tidal volume) can be supplied to the patient. These pressures P1 and P2 of the pressure interval are determined in particular based on the respective compliance of the ventilated patient.

In this regard, it is noted that generally two types of compliance are known, on the one hand static compliance and on the other hand dynamic compliance. To determine the static compliance, a (fixed) volume of fluid, starting from a pressure P1, is supplied to an airway. This state is subsequently maintained until a pressure P2 results. In contrast, dynamic compliance is determined during continuous ventilation. After the (fixed) volume of fluid is supplied, the pressure P2 then present is immediately measured. The pressure interval P1, P2 for dynamic compliance is therefore generally greater than or equal to the pressure interval for static compliance. The compliance is represented as a curve in a pressure-volume diagram (or volume-pressure diagram, since the compliance is generally a ratio of V/P that varies with changing pressure).

Thus, in particular during at least one ventilation process (inhalation, i.e., supplying fluid, and exhalation, i.e., discharging fluid, to/from the airway), the profile of the compliance curve is determined or additionally estimated (based on empirical values, for example). In particular, it is specifically the subregion of the compliance curve in which a given volume V (optionally $V_T$) can be supplied in the smallest possible pressure interval that is determined.

In particular, in order to determine the profile of the compliance curve, a volume of fluid, preferably a small volume delta V of at most 100 mL, particularly preferably at most 50 mL, is supplied to the at least one airway via the fluid supply unit. During and/or preferably after supplying this volume, the change in pressure delta P in the at least one airway is measured and a value for the compliance is determined. At least the profile of the subregion of the compliance curve is then estimated, taking into consideration either empirical values or, if appropriate, values that have already been determined for the compliance of this patient. Alternatively, further (small) volumes delta V are supplied and the respective change in pressure delta P is determined. From these values for the compliance, the profile of at least the subregion of the compliance curve can be determined and/or estimated (with increasing accuracy). In addition, the profile of the compliance curve and the preferred position of a pressure interval, provided for the subsequent ventilation of the patient, with the pressures P1 (in particular PEEP) and P2 (in particular PIP) can be determined or estimated based on decreasing or increasing absolute values of the compliance.

$V=f_{CP}(P)$ applies in a pressure-volume diagram and $P=f_{CV}(V)$ applies in a volume-pressure diagram, where $V=f_{CP}(P)$ and $P=f_{CV}(V)$ represent the function that describes the curve (i.e., the compliance) in the respective diagram.

In particular, at least one of the following variables may be preset or determined in advance: PEEP, respiratory rate, volumetric flow rate, I/E, resistance of the at least one airway, so that the required tidal volume $V_T$ may be supplied under the criterion of the smallest possible energy input. In addition, any of these variables may be further adjusted after determining and evaluating the ventilation process, so that a predetermined tidal volume $V_T$ is supplied under the parameters that are then set.

A fluid supply unit and a fluid discharge unit include at least one (shared) source of compressed gas or a device with which a fluid (for example, a gas or a gas mixture that is suitable for ensuring the ventilation of a patient) can be introduced into and removed from the at least one airway of the patient. Preferably, only one source of compressed gas is present, or the exhalation also takes place via a ventilation device, such as a gas flow reversing device as mentioned at the outset, wherein the fluid is supplied to the airway via a lumen and is discharged again via the same lumen.

The control device is suitable in particular for determining or additionally for estimating a profile of at least one subregion of a compliance curve. The determination of the compliance curve takes place during ventilation by supplying and/or discharging the fluid to/from the at least one airway and by determining at least one value of the compliance. The profile of the compliance curve of a patient may be estimated in particular taking into consideration the at least one value of the compliance.

The compliance may be determined in particular at time intervals, or determined repeatedly after a certain number of ventilations.

In particular, the control device utilizes the measured values of at least one pressure sensor and monitors the volumetric flows that are supplied via the fluid supply unit and discharged via the fluid discharge unit.

In particular, the pressure present in the respective airway is monitored and/or measured and computationally estimated or determined. A pressure sensor is thus preferably arranged in the airway so that in particular a continuous pressure measurement in the airway is possible, even during the ventilation. The pressure sensor may also be situated outside the airway, at the fluid supply unit or the fluid discharge unit.

Such an arrangement of a pressure sensor is particularly advantageous in determining the profile of the compliance curve, since in this case the (respectively) changing pressure delta P in the airway can be determined during the continuous or staged supply of a volume or of partial volumes of the fluid.

During the ventilation of the patient, an active control of the fluid that is supplied during the inhalation of the lung of the patient and discharged during the exhalation from the lung of the patient by the ventilation device preferably takes place continuously (i.e., occurring at any point in time). The active control encompasses a continuous change in pressure of the fluid that is supplied and discharged by the ventilation device. The continuously changed pressure is in particular the pressure inside the at least one airway, and thus in particular inside the lung. This pressure may be determined by a sensor via a measurement at the end of a ventilation device, such as a catheter, that reaches into the airway.

The continuous pressure change results in particular in continuous control of the fluid supply rate and fluid discharge rate [milliliter/second] through the ventilation device to the lung or from the lung during the ventilation processes. In particular, the fluid volume (volume V) present in the lung is thus continuously changed. During the change in the fluid volume present in the lung, the fluid supply rate and/or the fluid discharge rate through the ventilation device to the lung or from the lung are/is preferably not changed, and thus remain(s) essentially constant. The fluid supply rate does not necessarily have to correspond to the fluid discharge rate, although it can also be of the same absolute value. Moreover, the fluid supply rate may be varied from one inhalation process to the following inhalation process. The same applies, in particular independently thereof, for the fluid discharge rate during successive exhalation processes.

In particular, states are avoided in which there is no change in the pressure and in particular no change in the fluid volume present in the lung within a time interval. Such time intervals in which there is no change in the pressure and/or in particular no change in the fluid volume present in the lung are preferably at most 0.5 s [second], in particular at most 0.2 s, preferably at most 0.1 s, in length, and in particular concern (solely) the point in time of fluid flow reversal (i.e., the transition from fluid supply to fluid discharge, and vice versa).

The pressure is in particular measured in the patient him/herself, particularly advantageously in the region of the outflow from the ventilation device, i.e., from a lumen (tube/catheter) transporting the fluid into the airway of the patient. Alternatively and/or additionally, the pressure is measured in the ventilation device.

In particular, the pressure in the ventilation device does not correspond to the pressure in the airway of the patient. In particular, a continuous change in the pressure in the airways may also be set by an at least intermittently constant pressure in the ventilation device.

A change in the pressure in the airways may in particular also still be measured when a fluid supply rate or fluid discharge rate is zero. This change results in particular from the properties of the airways themselves. A fluid supply rate and fluid discharge rate of zero should be avoided if at all possible (at most for time intervals of up to 0.5 s, in particular at most 0.2 s or 0.1 s, and then also only at the point in time of fluid flow reversal; if appropriate, longer time intervals of up to 2.0 s are possible, for example in order to carry out a pressure measurement, wherein such an extended time interval is provided only at intervals of at least 30 s, in particular at least 2 minutes, preferably at least 5 minutes). For this purpose, the fluid supply rate and fluid discharge rate are in particular predefined (solely) by the ventilation device, wherein the pressure in the airways is monitored.

In particular, a sinusoidal or sawtooth-shaped breathing pattern (pressure [millibar] over time [second]) is thus set, wherein a slope of the curve (pressure over time) is continuously not equal to zero, and has a slope equal to zero in particular only at the point in time of fluid flow reversal for a time interval of at most 0.5 s [second], in particular at most 0.2 s, preferably at most 0.1 s, particularly preferably never.

In particular, a breathing pattern is predefined for the patient preferably at all times during the ventilation by the ventilation device; i.e. the fluid supply rate (inhalation flow) and fluid discharge rate (exhalation flow) are controlled and determined (solely) by the ventilation device (and not by the patient).

In particular, the fluid supply and, if appropriate, additionally the fluid discharge take place exclusively via the ventilation device or via at least one lumen inserted into the airways of the patient.

The continuous change in pressure ensures that the fluid supply and fluid discharge do not take place too quickly or too slowly, and it is thus possible to prevent or at least minimize damage to the airways and in particular to the lung tissue.

Furthermore, the fluid supply and fluid discharge may take place, for example, taking into consideration compliance of the airways at advantageous pressure intervals (i.e., between a first, higher pressure and a second, lower pressure) and at a predefinable ventilation frequency.

Reference is made to previously unpublished DE 10 2016 109 528.1 with regard to determining the compliance, and a ventilation device and a method for operating a ventilation device, each of which concerns compliance during ventilation.

In particular, the ventilation process is settable in such a way that
  a) while supplying the fluid, a first volume that is present at the pressure $P_0$, and while discharging the fluid, a second volume that is present at the same pressure $P_0$, differs at most by 30%, in particular at most by 20%, preferably at most by 10%, from the volume interval that is present in the pressure interval or b) while supplying the fluid, a first pressure that is present at the volume $V_0$, and while discharging the fluid, a second pressure that is present at the same volume $V_0$, differs at most by 30%, in particular at most by 20%, preferably at most by 10%, from the pressure interval that is present in the volume interval.

It is preferred that a) the ventilation process is settable over at least 60%, in particular at least 80%, of the pressure interval in such a way that while supplying the fluid, a first volume that is present at the pressure $P_0$, and while discharging the fluid, a second volume that is present at the same pressure $P_0$, differs at least by 1%, preferably at least by 3%, from the volume interval that is present in the pressure interval or b) the ventilation process is settable over at least 60%, in particular at least 80%, of the volume interval in such a way that while supplying the fluid, a first pressure that is present at the volume $V_0$, and while discharging the fluid, a second pressure that is present at the same volume $V_0$, differs at least by 1%, preferably at least by 3%, from the pressure interval that is present in the volume interval.

In particular, the control device is suitable a) for determining integrals $f_{ZP}(P)$ and $f_{AP}(P)$ in the pressure interval and for determining a difference between $\int f_{ZP}(P)\, dP$ and $\int f_{AP}(P)\, dP$ in the pressure interval or b) for determining integrals $f_{ZV}(V)$ and $f_{AV}(V)$ in the volume interval and for determining a difference between $\int f_{ZV}(V)\, dV$ and $\int f_{AV}(V)\, dV$ in the volume interval.

In particular, the difference between the integrals $f_Z(P)$ and $f_A(P)$ in the pressure interval is regarded as a measure for the energy absorbed by the airway. This difference between the integrals should therefore be as small as possible, so that the energy absorbed by the airway may be regarded to be as low as possible.

In particular, the control device is suitable for carrying out multiple ventilation processes, in which the difference between a) $\int f_{ZP}(P)\, dP$ and $\int f_{AP}(P)\, dP$ in the pressure interval or b) $\int f_{ZV}(V)\, dV$ and $\int f_{AV}(V)$ in the volume interval is controllable, wherein a ratio of the difference to a critical difference that is established for a given patient is settable.

In particular, a critical difference may be determined for a patient, for example based on empirical values or a determination of compliance of the airway. This critical difference refers to the amount of energy that may be supplied to the at least one airway during a ventilation process without the expectation of damage (VILI) to the at least one airway. The critical difference may be, for example, the difference between the integrals of $\int f_{ZP}(P)\, dP$ and of $\int f_{AP}(P)\, dP$ in the pressure interval, where $f_{ZP}(P)$ describes the supplying of the fluid with the highest possible compliance, and $f_{AP}(P)$ describes the discharge of the fluid due to passive exhalation (i.e., (solely) the energy stored in the elastic tissue elements of the lung and thorax drives the exhalation).

In particular, the integrals of $\int f_{ZP}(P)\, dP$ and $\int f_{AP}(P)\, dP$ in the pressure interval determine the area below the first curve section and the area below the second curve section, respectively (the same applies for $\int f_{ZV}(V)\, dV$ and $\int f_{AV}(V)$ in the volume interval). A difference between the integrals $\int f_{ZP}(P)\, dP$ and $\int f_{AP}(P)\, dP$ in the pressure interval thus denotes the area enclosed by the first curve section and the second curve section. The difference between the integrals $\int f_{ZP}(P)\, dP$ and $\int f_{AP}(P)\, dP$ in the pressure interval, and thus the area enclosed by the curve sections, is regarded as a measure for the energy absorbed by the airway. This difference between the integrals, i.e., this area, should therefore be as small as possible, so that the energy absorbed by the airway may be regarded to be as low as possible.

Furthermore, a (second) ventilation device having a visualization apparatus is proposed, the ventilation device being suitable for ventilating a patient. The ventilation device having a visualization apparatus comprises at least a fluid supply unit and a fluid discharge unit that are suitable for respectively supplying a fluid into at least one airway, i.e., into a lung part or into the lung, of a patient and for discharging the fluid from this airway; and further comprises a control device which, at least during a ventilation process of the at least one airway, i.e., the at least one-time supply of the fluid into the at least one airway and the at least one-time discharge of the fluid from the at least one airway by operating the ventilation device, is suitable for determining a profile of at least one volume-pressure curve in a volume-pressure diagram. The curve has a first curve section $V=f_{ZP}(P)$ or $P=f_{ZV}(V)$ and a second curve section $V=f_{AP}(P)$ or $P=f_{AV}(V)$, wherein the first curve section represents the profile of the supplied volume and of the pressure while supplying the fluid into the at least one airway, and the second curve section represents the profile of the discharged volume and of the pressure while discharging the fluid from the at least one airway; wherein the ventilation process takes place within a pressure interval and within a volume interval. The control device is suitable for determining an area, this area in the volume-pressure diagram being enclosed by the first curve section and the second curve section of the one ventilation process; wherein at least one of the following parameters may be visually discernibly displayed via the visualization apparatus:

a) a measure for a size of the area; or b) a measure for a change in the area over multiple ventilation processes; or c) a measure for a ratio of the area to a critical area that is established for a given patient (i.e., the critical difference of the integrals); or d) a measure for a change in the ratio of the area to a critical area that is established for a given patient (i.e., the critical difference of the integrals) over multiple ventilation processes.

In particular, in addition the profile of at least one volume-pressure curve in a volume-pressure diagram is displayable via the visualization apparatus. The curve has a first curve section $V=f_{ZP}(P)$ or $P=f_{ZV}(V)$ and a second curve section $V=f_{AP}(P)$ or $P=f_{AV}(V)$, wherein the first curve section represents the profile of the supplied volume and of the pressure while supplying the fluid into the at least one airway, and the second curve section represents the profile of the discharged volume and of the pressure while discharging the fluid from the at least one airway.

In particular, the visualization apparatus includes a graphical display area, such as a monitor, via which the stated parameters may be displayed for readout.

In particular, the stated parameters may be illustrated, for example, by a type of "traffic light display." The values of the parameters may be assigned to zones that are displayable in appropriate colors (for example, green for "noncritical"; yellow for an "intermediate area"; red for "critical").

At least one of the parameters a. through d. is preferably displayable in relation to at least one intervention limit. "Intervention limits" are in particular certain values of the parameters; when the intervention limit is reached, for example an intervention or a control may be necessary. This means in particular that when a parameter reaches a certain value, an indication is provided via the visualization apparatus, so that an operator of the ventilation device or the control device itself is notified of this circumstance, or if necessary may make a change in the parameter.

In addition, a (first) method for operating a (first or second) ventilation device is proposed which is provided for ventilating a patient, wherein the ventilation device comprises at least a fluid supply unit and a fluid discharge unit that are suitable for respectively supplying a fluid into at least one airway, i.e., into a lung part or into the lung, of a patient and for discharging the fluid from this airway; and further comprises a control device. The method comprises at least the following steps:

a) carrying out a ventilation process, including at least a one-time supply of a fluid into at least one airway, i.e., a lung part or the lung, of the patient and at least a one-time discharge of the fluid from this airway by operating the ventilation device; wherein the ventilation process takes place within a pressure interval and within a volume interval;

b) determining or setting a profile of at least one volume-pressure curve in a volume-pressure diagram by the control device during the ventilation process; wherein the curve has a first curve section $V=f_{ZP}(P)$ or $P=f_{ZV}(V)$ and a second curve section $V=f_{AP}(P)$ or $P=f_{AV}(V)$, wherein the first curve section represents the profile of the supplied volume V and of the pressure P while supplying the fluid into the at least one airway, and the second curve section represents the profile of the discharged volume V and of the pressure P while discharging the fluid from the at least one airway; wherein by use of the control device the ventilation process is set in such a way that    (1) over at least 60%, in particular at least 80%, of the pressure interval, a ratio of an absolute value of a first slope of the first curve section at a pressure $P_0$, i.e., $df_{AP}/d(P)\,(P_0)$, and an absolute value of a second slope of the second curve section, i.e., $df_{AP}/d(P)\,(P_0)$, at the same pressure $P_0$, has a value of at least 0.5 and at most 2.0, in particular at least 0.67 and at most 1.5, or    (2) over at least 60%, in particular at least 80%, of the volume interval, a ratio of an absolute value of a first slope of the first curve section at a volume $V_0$, i.e., $df_{AV}/d(V)\,(V_0)$, and an absolute value of a second slope of the second curve section, i.e., $df_{AV}/d(V)\,(V_0)$, at the same volume $P_0$, has a value of at least 0.5 and at most 2.0, in particular at least 0.67 and at most 1.5.

In particular, the ventilation process is settable in such a way that over at least 60%, in particular at least 80%, of the pressure interval the ratio has a value of at least 0.75 and at most 1.25.

In particular, the control device determines a profile of a volume-pressure curve in a volume-pressure diagram during the ventilation process for compliance of the airway according to one of $V=f_{CP}(P)$ or $P=f_{CV}(V)$; wherein the ventilation process in steps a) and b) is set in such a way that over at least 60%, in particular at least 80%, of the pressure interval, or over at least 60%, in particular at least 80%, of the volume interval, a ratio of    each of $df_{AP}/d(P)\,(P_0)$, $df_{ZP}/d(P)\,(P_0)$ and an absolute value of a measure of the change in the first volume of the compliance that is present at a pressure $P_0$ (11), i.e., $df_C/d(P)\,(P_0)$, or a ratio of
   each of $df_{AV}/d(V)\,(V_0)$, $df_{ZV}/d(V)\,(V_0)$ and an absolute value of a measure of the change in the first pressure of the compliance that is present at a volume $V_0$, i.e., $df_{CV}/d(V)\,(V_0)$ has a value of at least 0.5 and at most 2.0, in particular at least 0.67 and at most 1.5, preferably at least 0.75 and at most 1.25.

In particular, in step b) or in a further step c) the control device carries out a determination or a setting of an area; wherein this area in the volume-pressure diagram is enclosed by the first curve section and the second curve section of the one ventilation process.

In the at least one ventilation process, a ratio of the area to a critical area that is established for a given patient (the critical difference of the integrals) is preferably set.

In particular, the ventilation device includes a visualization apparatus, wherein at least one of the following parameters is visually discernibly displayed via the visualization apparatus:

a) a measure for a size of the area; or b) a measure for a change in the area over multiple ventilation processes; or    c) a measure for a ratio of the area to a critical area that is established for a given patient (i.e., the critical difference of the integrals); or    d) a measure for a change in the ratio of the area to a critical area that is established for a given patient (i.e., the critical difference of the integrals) over multiple ventilation processes.

In particular, the ventilation process is settable in such a way that a) while supplying the fluid, a first volume that is present at the pressure $P_0$, and while discharging the fluid, a second volume that is present at the same pressure $P_0$, differs at most by 30%, in particular at most by 20%, preferably at most by 10%, from the volume interval that is present in the pressure interval or    b) while supplying the fluid, a first pressure that is present at the volume $V_0$, and while discharging the fluid, a second pressure that is present at the same volume $V_0$, differs at most by 30%, in particular at most by 20%, preferably at most by 10%, from the pressure interval that is present in the volume interval.

The statements concerning the ventilation device and the ventilation device having a visualization apparatus are likewise transferable to the proposed method, and vice versa.

In particular, an (optionally additional) (second) method for operating an (above-described) ventilation device is proposed. The ventilation device is provided for ventilating a patient. The method comprises at least the following steps:

i. supplying a fluid into at least one airway, i.e., a lung part or the lung, of the patient and/or discharging the fluid from this airway by operating the ventilation device;

ii. determining or additionally estimating a profile of at least one subregion of a compliance curve of the at least one airway by the supplying and/or discharging of the fluid in step i. and determining at least one value of the compliance, wherein the following applies for the compliance C:

$$C = \text{delta } V / \text{delta } P \text{ [milliliter/millibar]};$$

wherein the compliance indicates how much fluid, i.e., a volume delta V [milliliter], is introduced into the at least one airway or is removed from the airway, so that a pressure in the airway changes by a pressure difference delta P [millibar];

iii. determining a position of a pressure interval with the pressures P1 and P2 along the profile of the at least one subregion of the compliance curve determined or additionally estimated in step ii., wherein an absolute value of the compliance is as large as possible for a ventilation process, i.e., an inhalation and/or an exhalation, carried out in this pressure interval;

iv. supplying and/or discharging the fluid within the pressure interval, determined in step iii., in at least one ventilation process subsequent to step iii.

In particular, this method having steps i. through iv. is additionally carried out, and optionally simultaneously or in a time-delayed manner, with respect to the method having steps a) and b). The compliance of the airway may be determined in particular during the supply of the fluid, and the supply and discharge of the fluid for at least one ventilation process take place according to steps a) and b) of the method.

A method for ventilating a patient with the lowest possible energy input is thus proposed. The minimization of the energy input is also achieved by determining the lowest possible pressure at which a required breathing volume $V_T$ (tidal volume) can be supplied to the patient. These pressures P1 and P2 of the pressure interval may be determined, for example, based on the respective compliance of the ventilated patient.

In particular, in step ii. a plurality of values for the compliance is determined, at least during an inhalation or an exhalation in a ventilation process, so that in step iii., for at least one subsequent ventilation process the position of the pressure interval with the pressures P1 and P2 is determinable for which an absolute value of the compliance is as large as possible. In particular, the control device determines the values for the compliance continuously or at predetermined time intervals. Preferably at least 5, particularly preferably at least 10, values for the compliance are determined for each ventilation process.

Steps ii., iii., and iv. are preferably carried out continuously, so that for each subsequent ventilation process or for multiple successive ventilation processes, the position of the pressure interval is selectively redetermined with the pressures P1 and P2.

According to one preferred embodiment, at least one of the following parameters is determined, at least for the subsequent ventilation process, as a function of the position of the pressure interval determined in step iii. and of the pressure interval itself, as well as the compliance thus determined:

a breathing volume $V_T$ (tidal volume) [milliliter],
a pressure P1 (PEEP, for example) and a pressure P2 (PIP, for example) [millibar],
a ventilation frequency F [1/second]
I/E.

According to one advantageous embodiment, at least the pressure rise, i.e., delta P/delta t [millibar/second], during an inhalation is monitored and limited.

According to another advantageous embodiment, at least the pressure drop, i.e., delta P/delta t [millibar/second], during an exhalation is monitored and limited.

The pressure rise and the pressure drop are preferably monitored and limited.

In particular, the absolute value of the pressure rise or pressure drop is limited to at most 40 mbar/s [millibar/second], in particular at most 30 mbar/s, preferably at most 20 mbar/s, particularly preferably at most 10 mbar/s.

In particular, the patient is ventilated using a catheter having a cross section of at most 30 mm$^2$ [square millimeters], in particular at most 20 mm$^2$, for the passage of at least one fluid that is supplied during the inhalation.

In particular, with such a small cross section (with inhalation and exhalation exclusively via this lumen), the pressure rise can be limited during the inhalation but also during the exhalation.

In particular, a resistance (for example, a flow resistance or the like) may be provided in a fluid discharge unit, which limits and controls the pressure drop during the exhalation.

For the proposed ventilation devices and described methods, it is similarly the case in particular that a subregion of a compliance curve that is present for the at least one airway of the patient to be ventilated is initially determined and, if appropriate, additionally estimated. For this purpose, the pressure rise during the delivery of a defined volume V (for example, 50 or 100 mL [milliliter]; optionally also $V_T$) is measured.

Moreover, a PEEP level (i.e., the lower pressure of P1 and P2) is in particular subsequently determined. To determine the PEEP level with which the patient is subsequently to be ventilated, multiple ventilation processes may initially also be carried out, in each case with different PEEP levels.

Furthermore, a PIP level (i.e., the higher pressure of P1 and P2) is preferably determined. To determine the PIP level with which the patient is subsequently to be ventilated, multiple ventilation processes may initially also be carried out, in each case with different PIP levels.

In addition, a tidal volume $V_T$ anticipated for the patient in question is set. This tidal volume $V_T$ may be further adapted during the ventilation, for example based on monitoring of the $CO_2$ level. Alternatively or additionally, the $CO_2$ level may also be influenced by means of the frequency of the ventilation processes or by the volumetric flow rate.

In particular, the pressure rise and/or the pressure drop are/is controlled and monitored during the ventilation so that the shear stress acting on the at least one airway and the energy input are minimized.

In particular, the ventilation device and/or the method ensure(s) that an absolute value of the compliance during a ventilation process is as large as possible, or in other words, in particular that (1) the ventilation takes place in a pressure interval in which the supplied volume of the fluid is at a maximum, or (2) the supply or discharge of a predetermined volume V or of a tidal volume $V_T$ of the fluid takes place within a pressure interval that is as small as possible.

The invention relates to a further (third) method for ventilating a patient and/or for operating a ventilation device, in particular the ventilation device described above. The ventilation device is provided for ventilating a patient.

This (third) method is also directed to the ventilation of a patient, wherein the lowest possible energy input into the airways of the patient is to be achieved. According to the present method, the fluid supplied during the inhalation of the lung of the patient and discharged during the exhalation from the lung of the patient by the ventilation device is controlled actively and continuously (i.e., takes place at any point in time) during the ventilation of the patient. The active control encompasses a continuous pressure change of the supplied and discharged fluid by the ventilation device. The continuously changed pressure is in particular the pressure inside the airways and thus inside the lung. This pressure may be determined by a sensor via a measurement at the end of a ventilation device, such as a catheter, that reaches into the airway.

The continuous change in pressure results in particular in a continuous control of the fluid supply rate and fluid discharge rate [milliliter/second] through the ventilation device to the lung or from the lung during the ventilation processes. In particular, the fluid volume V present in the lung is thus continuously changed. During the change in the fluid volume present in the lung, the fluid supply rate and/or the fluid discharge rate through the ventilation device to the lung or from the lung are/is preferably not changed and thus remain(s) essentially constant. The fluid supply rate does not necessarily have to correspond to the fluid discharge rate, although it may also be of the same magnitude.

Moreover, the fluid supply rate may be varied from one inhalation process to the following inhalation process. The same applies, in particular independently thereof, for the fluid discharge rate during successive exhalation processes.

In particular, states are avoided in which there is no change in the pressure and in particular no change in the fluid volume present in the lung within a time interval. Preferably, such time intervals in which there is no change in the pressure and/or in particular no change in the fluid volume present in the lung are at most 0.5 s [second], in particular at most 0.2 s, preferably at most 0.1 s, in length and in particular concern (only) the point in time of the fluid flow reversal (i.e., the transition from fluid supply to fluid discharge, and vice versa).

The invention relates to a further (third) ventilation device for ventilating a patient. The ventilation device comprises at least a fluid supply unit and a fluid discharge unit that are suitable for respectively supplying a fluid into at least one airway, i.e., into a lung part or into the lung, of a patient and for discharging the fluid from this airway; and further comprises a control device that, at least during a ventilation process of the at least one airway, i.e., the at least one-time supply of the fluid into the at least one airway and the at least one-time discharge of the fluid from the at least one airway by operating the ventilation device, is configured for setting a profile of a pressure P in the airway and a profile of a volume V of the fluid that is supplied to the airway and discharged from the airway according to $V=f_{ZP}(P)$ and $V=f_{AP}(P)$ or according to $P=f_{ZV}(V)$ and $P=f_{AV}(V)$. The ventilation process takes place within a pressure interval and within a volume interval; wherein by use of the control device the ventilation process is settable in such a way that, while supplying the fluid and while discharging the fluid, a volumetric flow rate F(t) [L/min] (optionally varying over time) varies at most by 50%, in particular at most by 25%, with respect to an average volumetric flow rate FD in the ventilation process, at least for 80%, preferably for 90%, of the duration of the ventilation process.

The volumetric flow rate F(t) may in particular vary over time, wherein in particular a (preferably) constant volumetric flow rate F(t) (based on the absolute value) should be set. The average volumetric flow rate FD is determined by dividing the sum of the supplied and the discharged fluid (i.e., always a positive value) by the duration of the ventilation process. For setting and controlling the volumetric flow rate F(t), the average volumetric flow rate may also be determined based on the prior ventilation processes or based on the preset parameters (for example, frequency and tidal volume).

Within the scope of the present invention, it has been found that in particular a difference in the volumetric flow rate F(t) also affects the energy that is absorbed by the airway.

The invention relates to a further (fourth) ventilation device for ventilating a patient. The ventilation device having a visualization apparatus comprises at least a fluid supply unit and a fluid discharge unit that are suitable for respectively supplying a fluid into at least one airway, i.e., into a lung part or into the lung, of a patient and for discharging the fluid from this airway; and further comprises a control device that, at least during a ventilation process of the at least one airway, i.e., the least one-time supply of the fluid into the at least one airway and the at least one-time discharge of the fluid from the at least one airway by operating the ventilation device, is suitable for determining and setting a volumetric flow rate F(t) [L/min] of the fluid. The ventilation process takes place within a pressure interval and within a volume interval; wherein the control device, assuming an airway resistance R of the airway of the patient, is suitable for determining a power loss PW(t) [watt] of the airway according to $PW(t)=R_1*(F(t))^3+R_2*(F(t))^2$, where $R_1=R$ [pascal/(m$^3$/s)$^2$] and $R_2=R$ [pascal/(m$^3$/s)] (where the units are [pascal/(cubic meter/second)$^2$]) and [pascal/(cubic meter/second)], respectively); wherein at least one of the following parameters may be visually discernibly displayed via the visualization apparatus:

a) the power loss PW(t); or
b) an energy loss E [joule], namely, the integral of PW(t)dt, i.e., ∫PW(t)dt in a time interval; or
c) a measure for a ratio of the power loss PW(t) to a critical power loss that is established for a given patient; or
d) a measure for a ratio of the energy loss E to a critical energy loss that is established for a given patient.

The energy loss stated herein refers to the energy input into the airway mentioned at the outset. The aim is to minimize this energy loss. The airway resistance R, as mentioned above, may be determined by plethysmography, for example.

In particular, the visualization apparatus includes a graphical display area, such as a monitor, via which the stated parameters may be displayed for readout.

In particular, the stated parameters may be illustrated, for example, by a type of "traffic light display." The values of the parameters may be assigned to zones that are displayable in appropriate colors (for example, green for "noncritical"; yellow for an "intermediate area"; red for "critical").

At least one of the parameters a. through d. is preferably displayable in relation to at least one intervention limit. "Intervention limits" are in particular certain values of the parameters; when the intervention limit is reached, for example an intervention or a control may be necessary. This means in particular that when a parameter reaches a certain value, an indication is provided via the visualization apparatus, so that an operator of the ventilation device or the control device itself is notified of this circumstance, or if necessary may make a change in the parameter.

The invention relates to a (fourth) method for operating a ventilation device. The ventilation device is provided for ventilating a patient, wherein the ventilation device comprises at least a fluid supply unit and a fluid discharge unit that are suitable for respectively supplying a fluid into at least one airway, i.e., into a lung part or into the lung, of a patient and for discharging the fluid from this airway; and further comprises a control device. The method comprises at least the following steps:

a) carrying out a ventilation process, including at least a one-time supply of a fluid into at least one airway, i.e., a lung part or the lung, of the patient, and at least a one-time discharge of the fluid from this airway by operating the ventilation device; wherein the ventilation process takes place within a pressure interval and within a volume interval;

b) determining or setting a profile of a pressure P in the airway and a profile of a volume V of the fluid supplied to the airway and discharged from the airway according to $V=f_{ZP}(P)$ and $V=f_{AP}(P)$ or according to $P=f_{ZV}(V)$ and $P=f_{AV}(V)$; wherein by use of the control device the ventilation process is settable in such a way that, while supplying the fluid and while discharging the fluid, a volumetric flow rate F(t) [L/min] varies at most by 50%, in particular at most by 25%, with respect to an average volumetric flow rate FD in the ventilation process, at least for 80%, preferably for 90%, of the duration of the ventilation process.

In particular, the ventilation device includes a visualization apparatus, wherein at least one of the following parameters is visually discernibly displayed via the visualization apparatus:

a. the power loss PW(t); or
b. an energy loss E [joule], namely, the integral of PW(t)dt, i.e., ∫PW(t)dt in a time interval; or
c. a measure for a ratio of the power loss PW(t) to a critical power loss that is established for a given patient; or
d. a measure for a ratio of the energy loss E to a critical energy loss that is established for a given patient.

The invention relates to a further (fifth) ventilation device for ventilating a patient. The ventilation device comprises at least a fluid supply unit and a fluid discharge unit that are suitable for respectively supplying a fluid into at least one airway, i.e., into a lung part or into the lung, of a patient and for discharging the fluid from this airway; and further comprises a control device that, at least during a ventilation process of the at least one airway, i.e., the at least one-time supply of the fluid into the at least one airway and the at least one-time discharge of the fluid from the at least one airway by operating the ventilation device, is configured for setting a profile of a pressure P in the airway and a profile of a volume V of the fluid that is supplied to the airway and discharged from the airway according to $V=f_{ZP}(P)$ and $V=f_{AP}(P)$ or according to $P=f_{ZV}(V)$ and $P=f_{AV}(V)$, wherein the ventilation process takes place within a pressure interval and within a volume interval. By use of the control device, the ventilation process is settable in such a way that, while supplying the fluid and while discharging the fluid, the square of a speed $(s(t))^2$ of the profile of the pressure P [cm H$_2$O] and of the volume V [mL] i.e., $(s(t))^2=(dP/dt)^2+(dV/dt)^2$, varies at most by 300%, preferably at most by 200%, with respect to the average square of a speed sD$^2$ during the ventilation process, at least for 80%, preferably for 90%, of the duration of the ventilation process.

Within the scope of the present invention, it has been found that the power loss P(t) is proportional to the herein described square of a speed $(s(t))^2$ of the profile of the pressure P [cm H$_2$O] and the volume V [mL] while supplying the fluid and while discharging the fluid.

For this reason, in this case the square of a speed $(s(t))^2$ is determined that is calculable in particular via a control of the ventilation device.

The square of a speed $(s(t))^2$ may in particular vary over time; however, a (preferably) constant speed s(t) should specifically be set. The average square of a speed sD$^2$ is determined according to sD$^2$=(delta P/t)$^2$+(delta V/t)$^2$, where delta P is the pressure interval of the ventilation process, delta V is the volume interval of the ventilation process, and t is the duration of the ventilation process. For setting and controlling the ventilation process at a given moment, the average square of a speed may also be determined based on the prior ventilation processes or based on the preset parameters (for example, volumetric flow rate, PEEP, and PIP, as well as V$_T$ and frequency).

The invention relates to a further (sixth) ventilation device for ventilating a patient. The ventilation device having a visualization apparatus comprises at least a fluid supply unit and a fluid discharge unit that are suitable for respectively supplying a fluid into at least one airway, i.e., into a lung part or into the lung, of a patient and for discharging the fluid from this airway; and further comprises a control device which, at least during a ventilation process of the at least one airway, i.e., the at least one-time supply of the fluid into the at least one airway and the at least one-time discharge of the fluid from the at least one airway by operating the ventilation device, is suitable for determining a profile of at least one volume-pressure curve in a volume-pressure diagram; wherein the curve has a first curve section, $V=f_{ZP}(P)$ or $P=f_{ZV}(V)$, and a second curve section, $V=f_{AP}(P)$ or $P=f_{AV}(V)$, wherein the first curve section represents the profile of the supplied volume V and of the pressure P while supplying the fluid into the at least one airway, and the second curve section represents the profile of the discharged volume V and of the pressure P while discharging the fluid from the at least one airway; wherein the ventilation process takes place within a pressure interval and within a volume interval. The control device is suitable for determining the square of a speed $(s(t))^2$ of the profile of the pressure P [cm H$_2$O] and of the volume V [mL] while supplying the fluid and while discharging the fluid, i.e., $(s(t))^2=(dP/dt)^2+(dV/dt)^2$. At least one of the following parameters may be visually discernibly displayed via the visualization apparatus:

a) the square of the speed s(t), i.e., $(s(t))^2$; or
b) the integral of $(s(t))^2$dt, i.e., ∫$(s(t))^2$dt in a time interval; or
c) a measure for a ratio of the square of the speed $(s(t))^2$ to a critical speed squared that is established for a given patient; or
d) a measure for a ratio of the integral of $(s(t))^2$dt to a critical value of this variable that is established for a given patient.

In particular, the visualization apparatus includes a graphical display area, such as a monitor, via which the stated parameters may be displayed for readout.

In particular, the stated parameters may be illustrated, for example, by a type of "traffic light display." The values of the parameters may be assigned to zones that are displayable in appropriate colors (for example, green for "noncritical"; yellow for an "intermediate area"; red for "critical").

At least one of the parameters a. through d. is preferably displayable in relation to at least one intervention limit. "Intervention limits" are in particular certain values of the parameters; when the intervention limit is reached, for example an intervention or a control may be necessary. This means in particular that when a parameter reaches a certain value, an indication is provided via the visualization apparatus, so that an operator of the ventilation device or the control device itself is notified of this circumstance, or if necessary may make a change in the parameter.

The invention relates to a (fifth) method for operating a ventilation device. The ventilation device is provided for ventilating a patient, wherein the ventilation device comprises at least a fluid supply unit and a fluid discharge unit that are suitable for respectively supplying a fluid into at least one airway, i.e., into a lung part or into the lung, of a patient and for discharging the fluid from this airway; and further comprises a control device. The method comprises at least the following steps:

a) carrying out a ventilation process, including at least a one-time supply of a fluid into at least one airway, i.e., a lung part or the lung, of the patient and at least a one-time discharge of the fluid from this airway by operating the ventilation device; wherein the ventilation process takes place within a pressure interval and within a volume interval;

b) determining or setting a profile of at least one volume-pressure curve in a volume-pressure diagram by the control device during the ventilation process; wherein the curve has a first curve section, $V=f_{ZP}(P)$ or $P=f_{ZV}(V)$, and a second curve section, $V=f_{AP}(P)$ or $P=f_{AV}(V)$, wherein the first curve section represents the profile of the supplied volume V and of the pressure P while supplying the fluid into the at least one airway, and the second curve section represents the profile of the discharged volume V and of the pressure P while discharging the fluid from the at least one airway; wherein by use of the control device the ventilation process is settable in such a way that, while supplying the fluid and while discharging the fluid, the square of a speed $(s(t))^2$ of the profile of the pressure P [cm $H_2O$] and of the volume V [mL] i.e., $(s(t))^2=(dP/dt)^2+(dV/dt)^2$, varies at most by 300%, preferably at most by 200%, with respect to an average square of a speed $sD^2$ during the ventilation process, at least for 80%, preferably for 90%, of the duration of the ventilation process.

In particular, the ventilation device includes a visualization apparatus; wherein at least one of the following parameters is visually discernibly displayed via the visualization apparatus:

a) the square of the speed $s(t)$, i.e., $(s(t))^2$; or
b) the integral of $(s(t))^2 dt$, i.e., $\int (s(t))^2 dt$ in a time interval; or
c) a measure for a ratio of the square of the speed to a critical speed squared (33) that is established for a given patient; or
d) a measure for a ratio of the integral of $(s(t))^2 dt$ to a critical value of this variable (34) that is established for a given patient.

The statements concerning the ventilation devices (all, i.e., first through sixth) and the methods (all, i.e., first through fifth) are in each case transferable to the respective other subject matter of the present invention. In particular, with the ventilation device and the method the stated parameters and conditions may be combined with one another. In particular, at least one or some (or even all) of the stated parameters and conditions form (joint) criteria for a ventilation process (or a ventilation method that extends over multiple successive ventilation processes). In particular, a ventilation process should thus be carried out in such a way that it corresponds to all embodiments described for the different ventilation devices or methods.

It is expressly noted that the control device may also be claimed independently of the ventilation device. The control device is used in particular to regulate the ventilation processes. It establishes which variables are used to control the ventilation process and which parameters (maximum/minimum pressure, maximum/minimum volumetric flow rate, slope of the first and second curve sections, area, difference between the areas, etc.) are thereby monitored.

As a precaution, it is noted that the ordinal numbers used herein ("first," "second," "third," . . . ) are used primarily (only) to distinguish between multiple similar objects, variables, or processes; i.e., in particular no dependency and/or sequence of these objects, variables, or processes relative to one another are/is necessarily specified. If a dependency and/or sequence is necessary, this is explicitly indicated herein, or is readily apparent to those skilled in the study of the embodiment specifically described.

The invention and the technical field are explained in greater detail below with reference to the figures. It is pointed out that the figures show one particularly preferred embodiment variant of the invention, to which the invention, however, is not restricted. Identical components are denoted by the same reference numerals in the figures. In the figures, in each case schematically.

Figure 1:
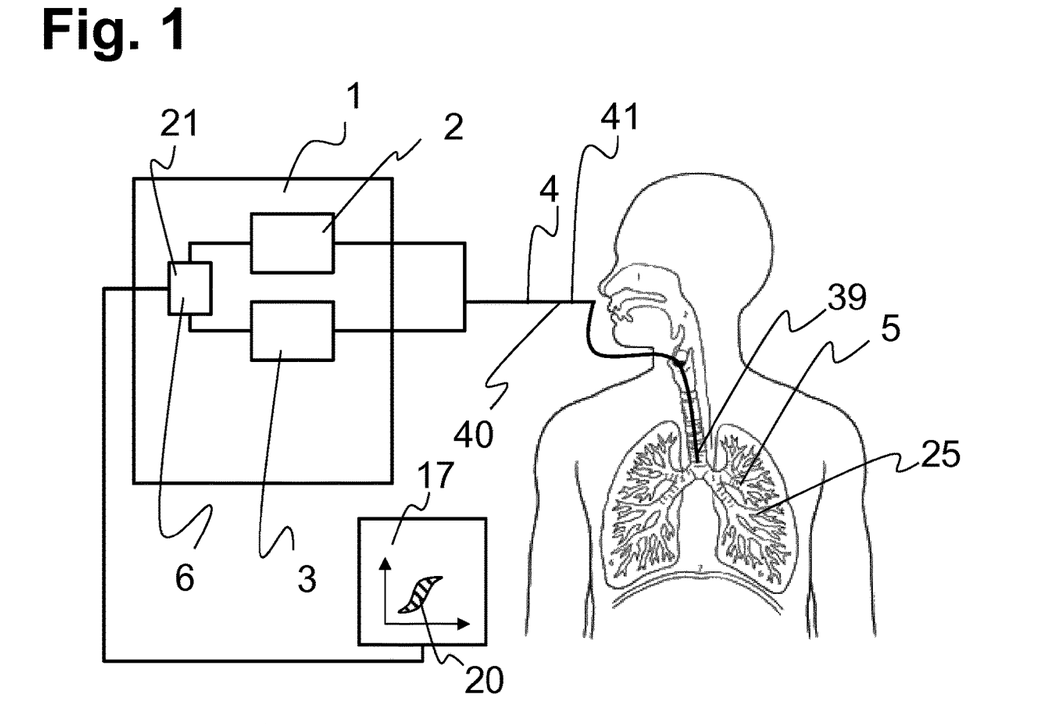
FIG. 1: shows a ventilation device and a patient.

FIG. 1 shows a ventilation device 1 and a patient with at least one airway 5, i.e., a lung. The ventilation device 1 comprises a fluid supply unit 2 and a fluid discharge unit 3 that are suitable for respectively supplying a fluid 4 into an airway 5, i.e., into a lung part or into the lung, of a patient and for discharging the fluid 4 from this airway 5. The ventilation device 1 further comprises a control device 6 which, during a ventilation of the at least one airway 5 of the patient, i.e., supplying a fluid 4 into the at least one airway 5 and/or discharging the fluid 4 from the at least one airway 5 by operating the ventilation device 1, is suitable for setting a profile of a pressure P7 in the airway 5 and a profile of a volume V8 of the fluid 4 that is supplied to the airway 5 and discharged from the airway 5 according to $V=f_{ZP}(P)$ and $V=f_{AP}(P)$. The ventilation device 1 is connected to the airway 5 of the patient via a catheter 40 of the lumen, with a lumen cross section 41 through which the fluid 4 can flow. The ventilation thus takes place, for example, via a single lumen, in particular using a gas flow reversing device.

The ventilation device 1 has a visualization apparatus 17, wherein at least one of the following parameters may be visually discernibly displayed via the visualization apparatus 17: a measure for a size of the area 20; or a measure for a change in the area 20 over multiple ventilation processes; or a measure for a ratio of the area 20 to a critical area 21 that is established for a given patient; or a measure for a change in the ratio of the area 20 to a critical area 21 that is established for a given patient over multiple ventilation processes.

A pressure sensor 39 is situated on the catheter 40 inside the airway 5. The airway 5 has a compliance C25.

Figure 2:
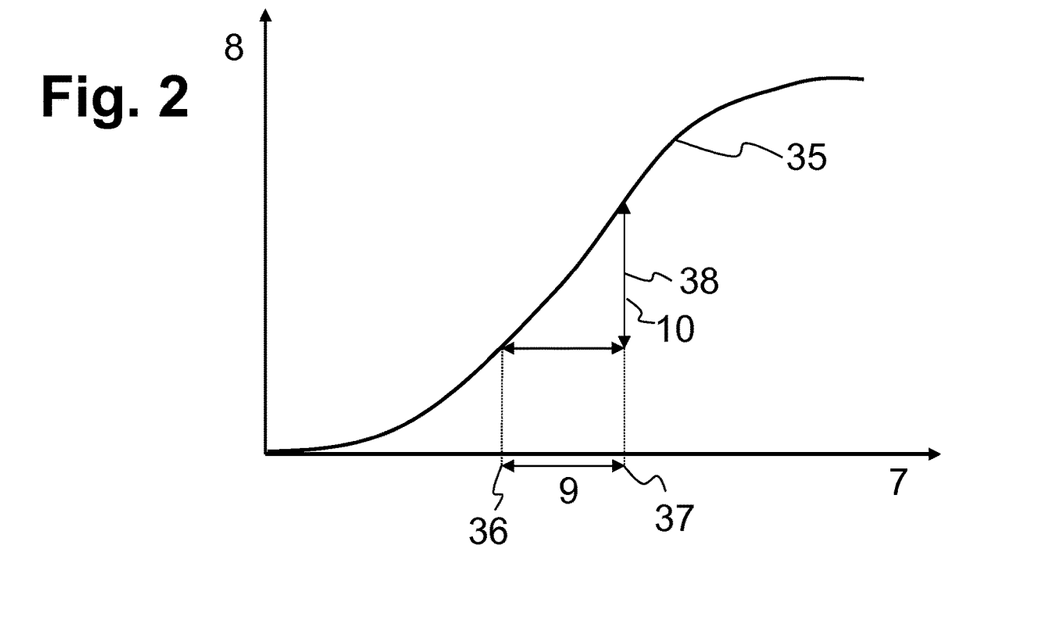
FIG. 2: shows a profile of a compliance curve.

FIG. 2 shows a profile of a compliance curve 35 in a pressure-volume diagram. The pressure 7 is plotted on the horizontal axis, and the volume 8 is plotted on the vertical axis. The profile of the compliance curve 35 is to be determined individually for each patient. In addition, the profile 7 may also change during a ventilation.

At least one value of the compliance 25 is initially determined within the scope of the method, i.e., by the ventilation device 1, where the following applies for the compliance C25: C=delta volume V8/delta P7 in milliliter/millibar. In the subregion of the compliance curve 35 shown here, the absolute value of the compliance 25 is at a maximum. By determining or estimating the profile of the compliance curve 25, the position of a pressure interval 9 with the pressures P1 36 and P2 37 may now be determined in which a tidal volume $V_T$ 38 of the fluid 4 can be supplied to the at least one airway 5. These pressures P1 36 and P2 37 are set on the ventilation device 1, so that at least one ventilation process, i.e., an inhalation and/or an exhalation, takes place in each case with a tidal volume $V_T$ 38 between these pressures P1 36 and P2 37.

Figure 3:
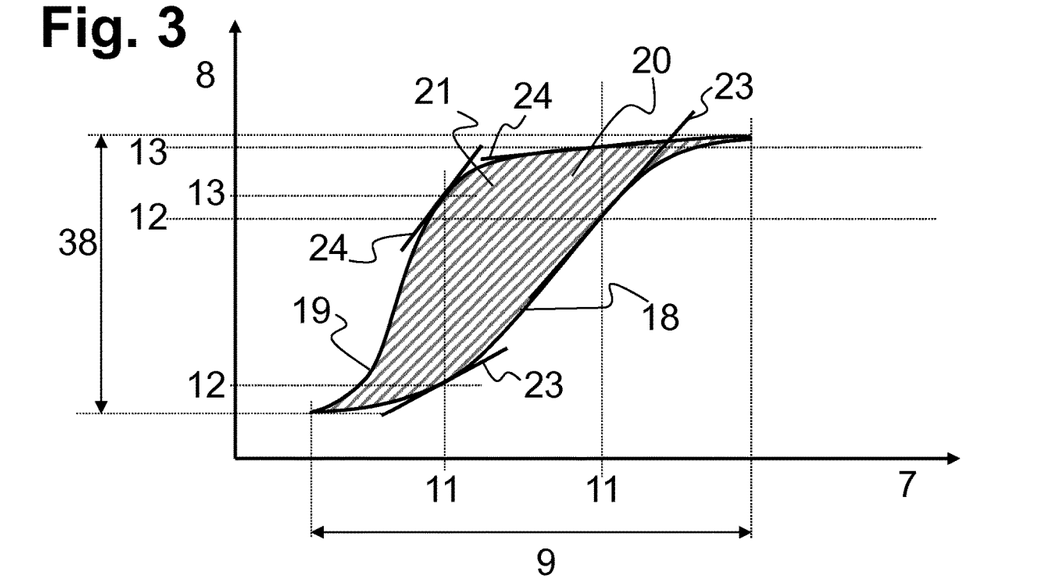
FIG. 3: shows a first illustration of a ventilation process in a volume-pressure diagram.

FIG. 3 shows a first illustration of a ventilation process in a volume-pressure diagram. The pressure 7 is plotted on the horizontal axis, and the volume 8 is plotted on the vertical axis. The illustrated volume-pressure curve shows the profile of the pressure P 7 in the airway 5 while the volume V8 in the airway 5 changes by the tidal volume $V_T$ 38, i.e., on the one hand by the supplied volume V8 of fluid 4, and on the other hand by the discharged volume V8 of fluid 4. The curve has a first curve section 18 $V=f_{ZP}(P)$ (the bottom curve extending from a lowest pressure 7 and a smallest volume 8 to a highest pressure 7 and a largest volume 8), and a second curve section 19 $V=f_{AP}(P)$ (the top curve extending next to the first curve section 18, from a highest pressure 7 and a largest volume 8 to a lowest pressure 7 and a smallest volume 8), wherein the first curve section 18 represents the profile of the supplied volume V8 (tidal volume $V_T$ 38) and of the pressure P7 while supplying the fluid 4 into the at least one airway 5, and the second curve section 19 represents the profile of the discharged volume V8 (tidal volume $V_T$ 38) and of the pressure P7 while discharging the fluid 4 from the at least one airway 5.

The measure of the change in the first volume 12 that is present at a pressure $P_0$ 11 is, for example, the first slope 23 of the volume-pressure curve, in the present case, of the first curve section 18, in a volume-pressure diagram. The slope (first slope 23 and second slope 24) is determined by the first derivative of the respective function $V=f_{ZP}(P)$ and $V=f_{AP}(P)$, i.e., $df_{AP}/d(P)(P_0)$ and $df_{ZP}/d(P)(P_0)$.

It has been found that the first slope 23 of a first curve section 18 at a pressure $P_0$ 11 of a volume-pressure curve, representable in a volume-pressure diagram, and the second slope 24 of a second curve section 19 (i.e., the absolute value of a measure of the change in a second volume 13, present at the same pressure $P_0$ 11, while discharging the fluid 4), at the same pressure $P_0$ 11 in each case (the pressure $P_0$ 11 lies within the pressure interval 9), should have approximately the same value in a largest possible range of the pressure interval 9.

The control device 6 on the one hand controls and monitors the pressure profile and volume profile while fluid 4 is supplied into the at least one airway 5. On the other hand, the discharge of the fluid 4 from the airway 5 is now also controlled and monitored as a function of the profile of this first curve section 18. In particular, no passive exhalation (see FIG. 3), which typically would produce a second curve section 19 that differed greatly from the first curve section 18, and thus a large area 20, is allowed here. In contrast, it is proposed for the control device 6 to also actively monitor and control the discharge of the fluid 4, wherein the second curve section 19 approximates the profile of the first curve section 18 (see FIG. 4).

Initial tests with these types of ventilation devices and methods have shown that damage to the at least one airway 5 (ventilator-induced lung injury (VILI)) may be at least reduced or even effectively prevented by such control of the ventilation.

The control device 6 is suitable for determining integrals $f_{ZP}(P)$ and $f_{AP}(P)$ in the pressure interval 9, and for determining a difference between $\int f_{ZP}(P)\,dP$ and $\int f_{AP}(P)\,dP$ in the pressure interval 9.

The control device 6 is suitable for carrying out multiple ventilation processes in which the difference between $\int f_{ZP}(P)\,dP$ and $\int f_{AP}(P)\,dP$ in the pressure interval 9 is controllable, wherein a ratio of the difference to a critical difference that is established for a given patient may be set.

Figure 4:
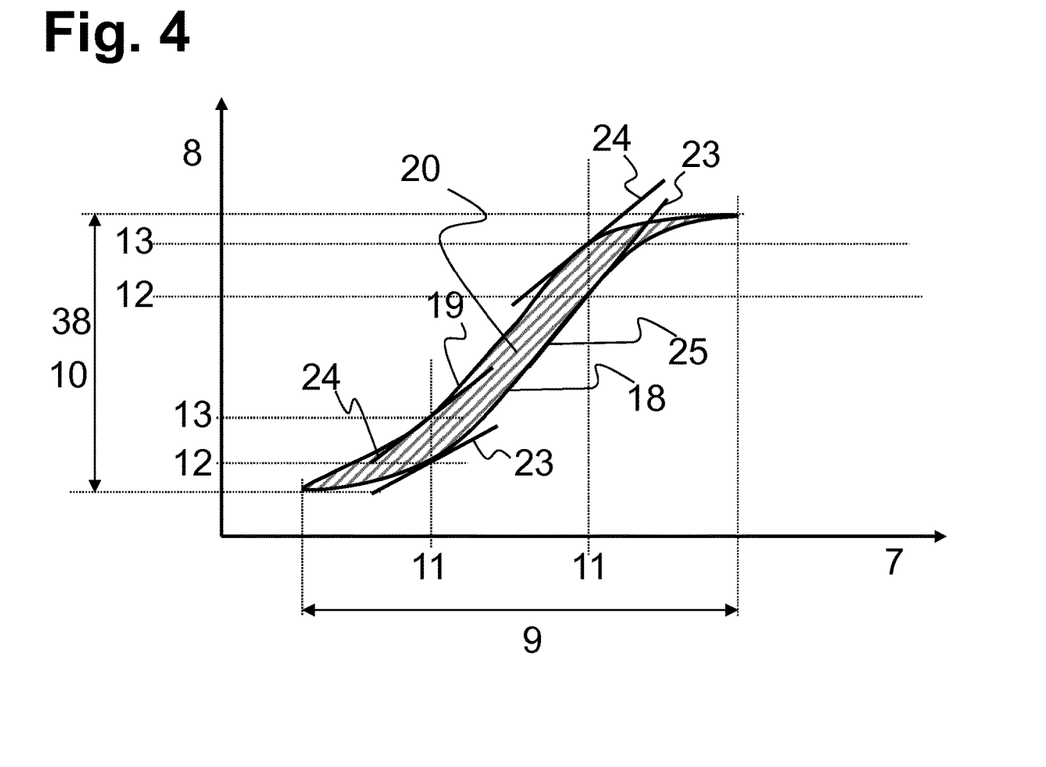
FIG. 4: shows a second illustration of a ventilation process in a volume-pressure diagram.

The area below the first curve section 18 and the area below the second curve section 19 is respectively determined by the integral of $\int f_{ZP}(P)$ and $f_{AP}(P)$, i.e., $\int f_{ZP}(P)\,dP$ and $\int f_{AP}(P)\,dP$, in the pressure interval 9. A difference between the integrals $f_{ZP}(P)$ and $f_{AP}(P)$ in the pressure interval 9 thus denotes the area 20 that is enclosed by the first curve section 18 and the second curve section 19. The difference between the integrals $f_{ZP}(P)$ and $f_{AP}(P)$ in the pressure interval 9, and thus, the area 20 enclosed by the curve sections 18, 19, is regarded as a measure for the energy E that is absorbed by the airway 5. This difference between the integrals, i.e., this area 20, should therefore be as small as possible so that the energy E absorbed by the airway 5 is as low as possible. FIG. 4 shows a ventilation process that is set in this way.

In particular, a critical difference, i.e., a critical area 21, may be determined for a patient based, for example, on empirical values or a determination of a compliance 25 of the airway 5. This critical difference or critical area 21 refers to the amount of energy E that may be supplied to the at least one airway 5 during a ventilation process without the expectation of damage (VILI) to the at least one airway 5. The critical difference may be, for example, the difference between the integrals of $f_{ZP}(P)$ and $f_{AP}(P)$ in the pressure interval 9, wherein $f_{ZP}(P)$, i.e., the first curve section 18 in the diagram according to FIG. 3, describes the supply of the fluid 4 with the highest possible compliance 25, and wherein $f_{AP}(P)$, i.e., the second curve section 19 in the diagram according to FIG. 3, describes the discharge of the fluid 4 due to passive exhalation (i.e., (only) the energy stored in the elastic tissue elements of the lung and thorax drives the exhalation). The critical difference in FIG. 3 is thus the critical area 21 between the curve sections 18, 19.

FIG. 4 shows a second illustration of a ventilation process in a volume-pressure diagram. Reference is made to the description for FIG. 3.

The control device 6, at least during the one shown ventilation process of the at least one airway 5, i.e., at least the one-time supply of the fluid 4 into the at least one airway 5 and the at least one-time discharge of the fluid 4 from the at least one airway 5 by operating the ventilation device 1, is configured for setting a profile of a pressure P7 in the airway 5 and a profile of a volume V8 of the fluid 4 supplied to the airway 5 and discharged from the airway 5 according to $V=f_{ZP}(P)$ and $V=f_{AP}(P)$. The ventilation process takes place within a pressure interval 9. By use of the control device 6, the ventilation process is settable in such a way that over at least 60% of the pressure interval 9, a ratio of an absolute value of a measure of the change in the first volume 12 that is present at a pressure $P_0$ 11 while supplying the fluid 4, i.e., $df_{AP}/d(P)(P_0)$ (first slope 23 of the first curve section 18 at the pressure $P_0$ 11), and an absolute value of a measure of the change in a second volume 13 that is present at the same pressure $P_0$ 11 while discharging the fluid 4, i.e., $df_{ZP}/d(P)$ ($P_0$) (second slope 24 of the second curve section 19 at the pressure $P_0$ 11), has a value of at least 0.5 and at most 2.0.

The same correspondingly applies for each volume $V_0$ 14 (not shown here), wherein over at least 60% of the volume interval 10, a ratio of an absolute value of a measure of the change in the first pressure 15 that is present at a volume $V_0$ 14 while supplying the fluid 4, i.e., $df_{AV}/d(V)$ ($V_0$), and an absolute value of a measure of the change in a second pressure 16 that is present at the same volume $V_0$ 14 while discharging the fluid 4, i.e., $df_{ZV}/d(V)$ ($V_0$), has a value of at least 0.5 and at most 2.0.

In this case, by use of the control device 6 the ventilation process is set in such a way that over at least a portion of the pressure interval 9, a ratio of an absolute value of a first slope of the first curve section 18 at a pressure $P_0$ 11, i.e., $df_{AP}/d(P)$ ($P_0$), and an absolute value of a second slope 24 of the second curve section 19, i.e., $df_{ZP}/d(P)$ ($P_0$), at the same pressure $P_0$ 11, has a value of at least 0.5 and at most 2.0. The absolute value of the result of the equation $[df_{AP}/d(P) (P_0)]/[df_{ZP}/d(P) (P_0)]$ should thus be at least 0.5 and at most 2.0. The pressure $P_0$ 11 is thus any pressure 7 within the pressure interval 9 or within a portion of the pressure interval 9.

The ventilation process is further set here in such a way that while supplying the fluid 4 a first volume 12 that is present at the pressure $P_0$ 11, and while discharging the fluid 4 a second volume 13 that is present at the same pressure $P_0$ 11, differ at most by 20% of the supplied or discharged volume 8 in the pressure interval 9.

The ventilation process is further set here in such a way that while supplying the fluid 4 a first volume 12 that is present at the pressure $P_0$ 11, and while discharging the fluid 4 a second volume 13 that is present at the same pressure $P_0$ 11, differ at least by 1% of the (overall) supplied or discharged volume 8 (the tidal volume $V_T$ 38 in this case) in the pressure interval.

At least one or some of the following parameters, for example, may be visually displayed via the visualization apparatus 17: a measure for a size of the area 20; a measure for a change in the area 20 over multiple ventilation processes; a measure for a ratio of the area 20 to a critical area 21 that is established for a given patient (i.e., the critical difference of the integrals); a measure for a change in the ratio of the area 20 to a critical area 21 that is established for a given patient (i.e., the critical difference of the integrals) over multiple ventilation processes. In addition, by use of the visualization apparatus 17 and based on the display, for example, of a ventilation process in a volume-pressure diagram according to FIG. 3 or FIG. 4, the slopes 23, 24 of the curve sections 18, 19 may be set or changed, either via the control device 6 or by an operator of the ventilation device 1.

FIG. 4 also shows that the control device 6 is configured for determining a profile of the pressure P7 in the airway 5 and a profile of a volume V8 of the fluid 4 that is supplied to the airway 5 and discharged from the airway 5 for a compliance 25 of the patient according to one of $V=f_{CP}(P)$ or $P=f_{CV}(V)$. The first curve section 18 corresponds to the compliance 25 here. The ventilation process may be set by the control device 6 in such a way that over at least 60% of the pressure interval 9, a ratio of each of $df_{AP}/d(P)$ ($P_0$) (in this case, the second slope 24 of the second curve section 19), $df_{ZP}/d(P)$ ($P_0$) (in this case, the first slope 23 of the first curve section 18) and an absolute value of a measure of the change in the first volume 12 of the compliance 25 that is present at a pressure $P_0$ 11, i.e., $df_{CP}/d(P)$ ($P_0$), has a value of at least 0.5 and at most 2.0.

Figure 5:
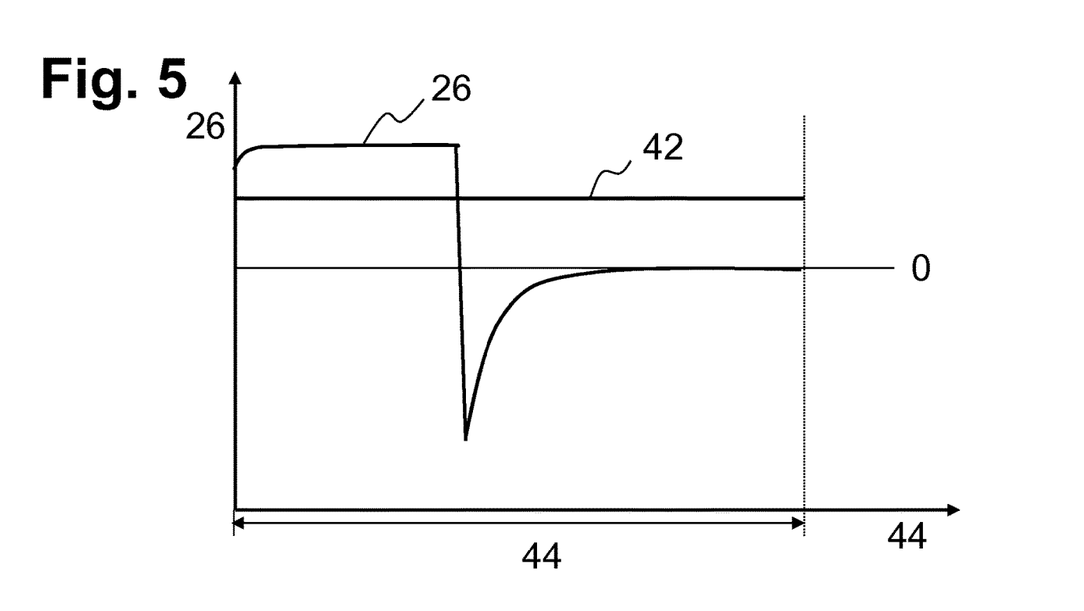
FIG. 5: shows a first diagram in which a volumetric flow rate is plotted with respect to time.
Figure 6:
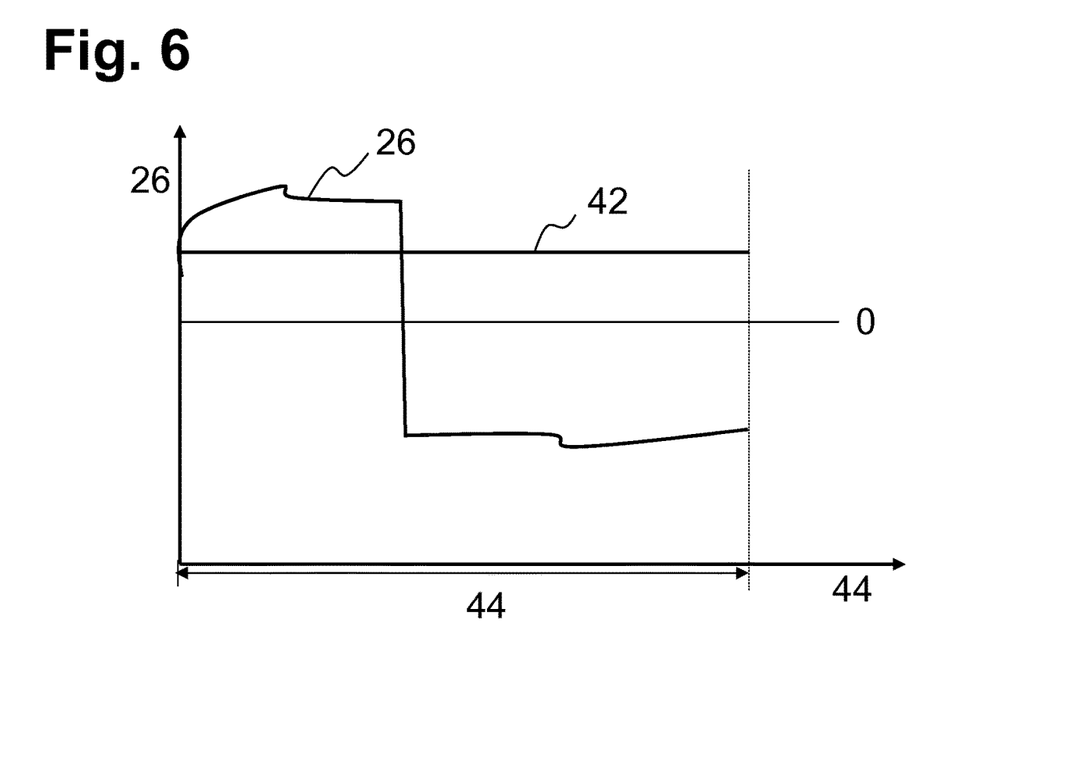
FIG. 6: shows a second diagram in which a volumetric flow rate is plotted with respect to time.

FIG. 5 shows a first diagram in which a volumetric flow rate 26 is depicted over time 44. FIG. 6 shows a second diagram in which a volumetric flow rate 26 is depicted over time 44. FIGS. 5 and 6 are described together in the following discussion.

The control device 6, as described above, is configured for setting a profile of a pressure P7 in the airway 5 and a profile of a volume V8 of the fluid 4 that is supplied to the airway 5 and discharged from the airway 5 according to $V=f_{ZP}(P)$ and $V=f_{AP}(P)$ or according to $P=f_{ZV}(V)$ and $P=f_{AV}(V)$, wherein the ventilation process takes place within a pressure interval 9 and within a volume interval 10. FIG. 5 shows the volumetric flow rate F(t) 26 of the ventilation process according to FIG. 3. FIG. 6 shows the volumetric flow rate F(t) 26 of the ventilation process according to FIG. 4. By use of the control device 6, the ventilation process is now settable (see FIG. 6) in such a way that while supplying the fluid 4 and while discharging the fluid 4, a volumetric flow rate F(t) 26 [L/min] (shown here with different algebraic signs and thus depicted as 0 L/min with respect to the zero line) varies at most by 50% with respect to an average volumetric flow rate FD 42 in the ventilation process, at least for 80% of a duration of the ventilation process. It is apparent that the volumetric flow rate F(t) 26 varies over time 44, wherein in particular a (preferably) constant volumetric flow rate F(t) 26 (based on the absolute value) should be set. The average volumetric flow rate FD 43 is determined by dividing the sum of the supplied and the discharged fluid 4 (i.e., always a positive value) by the duration of the ventilation process (i.e., the time 43 between the origin in the diagram and the vertical line). For setting and controlling the volumetric flow rate F(t) 26, the average volumetric flow rate FD 43 may also be determined based on the prior ventilation processes or based on the preset parameters (for example, frequency and tidal volume 38).

Figure 7:
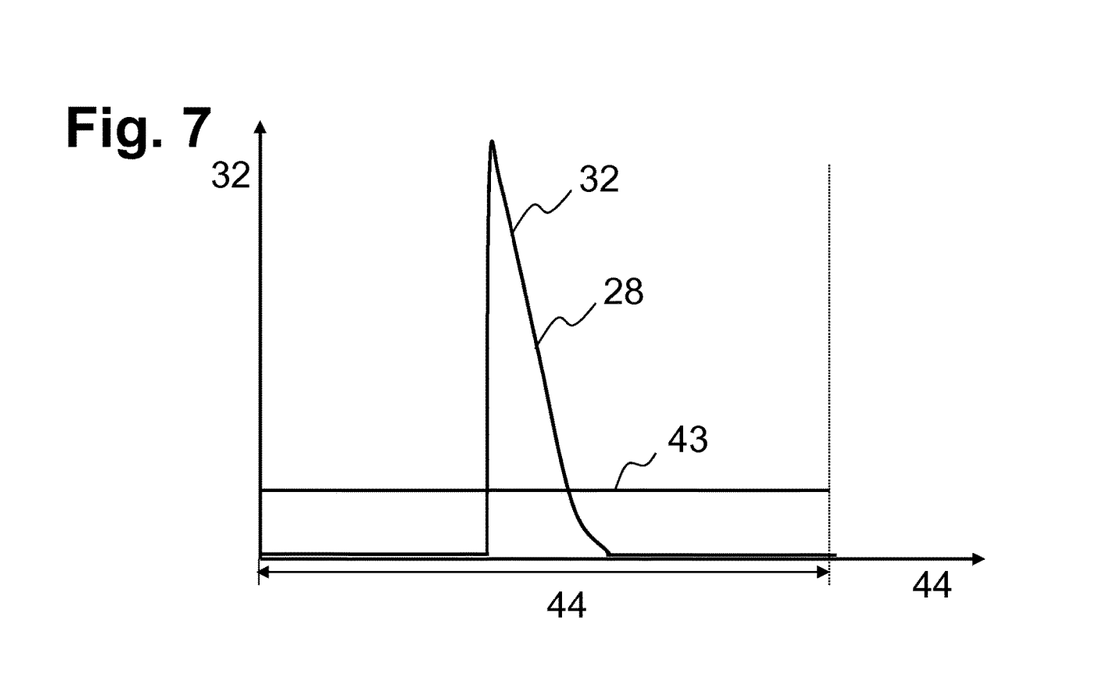
FIG. 7: shows a third diagram in which the square of a speed is plotted with respect to time.
Figure 8:
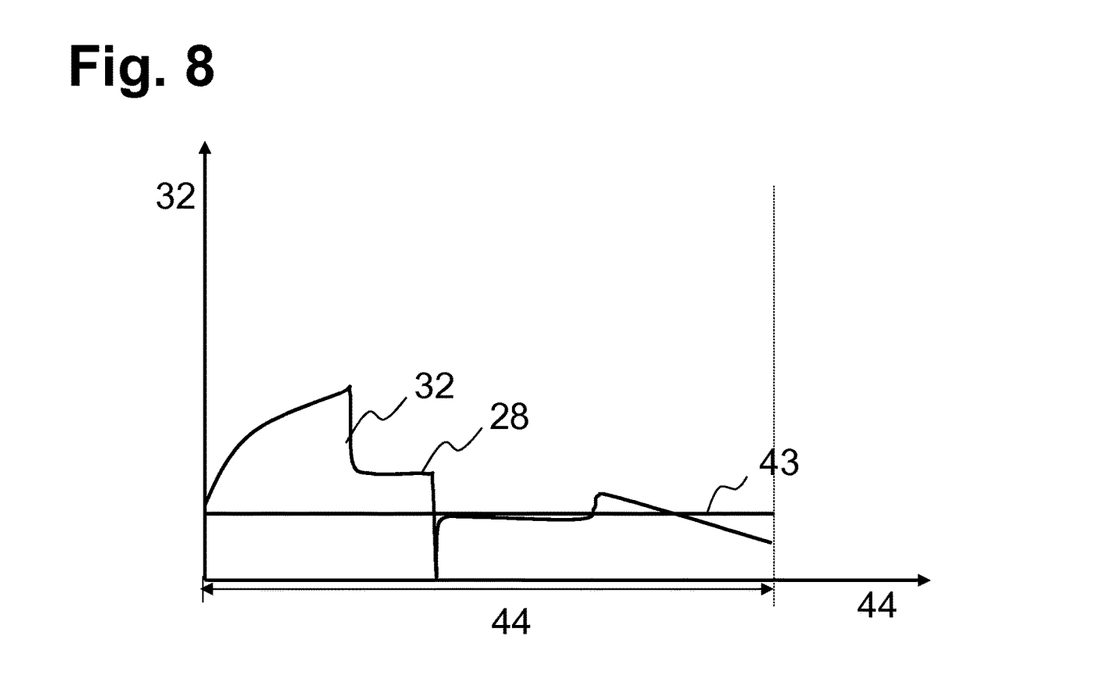
FIG. 8: shows a fourth diagram in which the square of a speed is plotted with respect to time.

FIG. 7 shows a third diagram in which the square of a speed over time 44 is illustrated. FIG. 8 shows a fourth diagram in which the square of a speed over time 44 is illustrated. FIGS. 7 and 8 are described together in the following discussion.

The control device 6, as described above, is configured for setting a profile of a pressure P7 in the airway 5 and a profile of a volume V8 of the fluid 4 that is supplied to the airway 5 and discharged from the airway 5 according to $V=f_{ZP}(P)$ and $V=f_{AP}(P)$ or according to $P=f_{ZV}(V)$ and $P=f_{AV}(V)$, wherein the ventilation process takes place within a pressure interval 9 and within a volume interval 10. FIG. 7 shows the square of a speed 32, i.e., $(s(t))^2$, of the ventilation process according to FIG. 3. FIG. 8 shows the square of a speed 32, i.e., $(s(t))^2$, of the ventilation process according to FIG. 4. By use of the control device 6, the ventilation process is settable in such a way that the square of a speed $(s(t))^2$ 32 of the profile of the pressure P7 and of the volume V8 while supplying the fluid 4 and while discharging the fluid 4, i.e., $(s(t))^2=(dP/dt)^2+(dV/dt)^2$, varies at most by 300% with respect to an average square of a speed $sD^2$ 43 during the ventilation process, at least for 80% of a duration of the ventilation process. It is apparent that in FIG. 7 a single maximum is present, and in FIG. 8 the square of the speed 32 has a more uniform profile. The units are not illustrated here. However, it has been found that in the ventilation technique described herein, a significantly reduced power loss 28 and thus a significantly lower energy loss 29 may be achieved during the ventilation process (time 44). The power loss PW(t) 28 corresponds to the profile of the square of a speed $(s(t))^2$ 32.

LIST OF REFERENCE NUMERALS 1 ventilation device
2 fluid supply unit
3 fluid discharge unit
4 fluid
5 airway
6 control device
7 pressure P
8 volume V
9 pressure interval
10 volume interval
11 pressure $P_0$
12 first volume
13 second volume
14 volume $V_0$
15 first pressure
16 second pressure
17 visualization apparatus
18 first curve section
19 second curve section
20 area
21 critical area
22 intervention limit
23 first slope
24 second slope
25 compliance C
26 volumetric flow rate F(t)
27 airway resistance
28 power loss PW(t)
29 energy loss E
30 critical power loss
31 critical energy loss
32 speed squared $(s(t))^2$
33 critical speed squared
34 variable
35 compliance curve
36 pressure P1
37 pressure P2
38 tidal volume $V_T$
39 pressure sensor
40 catheter
41 cross section
42 average volumetric flow rate
43 average square of a speed
44 time t

The invention claimed is:

1. Ventilation device for ventilating a patient, comprising:
at least a fluid supply unit configured for supplying a fluid into at least one airway of a patient;
a fluid discharge unit that is configured for discharging fluid from the at least one airway;
a control device which, during a ventilation process for the at least one airway, during at least a one-time supply of the fluid into the at least one airway and at least a one-time discharge of the fluid from the at least one airway by operating the ventilation device, is configured to set a profile of a pressure P in the airway and profile of a volume V of the fluid supplied to the airway and discharged from the airway according to $V=f_{zp}(P)$ and $V=f_{AP}(P)$, or according to $P=f_{2v}(V)$ and $P=f_{av}(V)$, wherein the ventilation process takes place within a pressure interval and within a volume interval;
wherein the ventilation process is configured to be set by the control device such that
a) over at least 60% of the pressure interval, a ratio of
an absolute value of a measure of a change in a first volume that is present at a pressure $P_0$ while supplying the fluid, i.e. $df_{AP}/d(P)(P_0)$ and
an absolute value of a measure of the change in a second volume that is present at the same pressure $P_0$ while discharging the fluid, i.e., $df_{ZP}/d(P)(P_0)$ or
b) over at least 60% of the volume interval, a ratio of
an absolute value of a measure of the change in a first pressure that is present at a volume V0 while supplying the fluid, i.e., $df_{AV}/d(V)(V_0)$ and
an absolute value of a measure of the change in a second pressure that is present at the same volume V0 while discharging the fluid, i.e. $df_{ZV}/d(V)(V_o)$,
has a value of at least 0.5 and at most 2.0.

2. Ventilation device according to claim 1, wherein the control device is configured for determining the profile of the pressure P in the airway and of the profile of the volume V of the fluid that is supplied to the airway and discharged from the airway for compliance of the patient according to one of V=fcp(P) or P=fcv(V), wherein the ventilation process is configured to be set by the control device such that
a) over at least 60% of the pressure interval, a ratio of
each of $df_{AP}/d(P)$ $(P_0)$, $df_{ZP}/d(P)$ $(P_0)$ and
an absolute value of a measure of the change in the first volume of the compliance that is present at a pressure $P_0$, i.e., $df_{CP}/d(P)$ $(P_0)$, or
b) over at least 60% of the volume interval, a ratio of
each of $df_{AV}/d(V)$ $(V_0)$, $df_{ZV}/d(V)$ $(V_0)$ and
an absolute value of a measure of the change in the first pressure of the compliance that is present at a volume $V_0$, i.e., $df_{CV}/d(V)$ $(V_0)$, has a value of at least 0.5 and at most 2.0.

3. Ventilation device according to claim 1, wherein the ventilation process is configured to be set by the control device such that over at least 60% of the pressure interval or 60% of the volume interval, the ratio has a value of at least 0.67 and at most 1.5.

4. Ventilation device according to claim 1, wherein the ventilation process is configured to be set by the control device such that over at least 60% of the pressure interval or 60% of the volume interval, the ratio is greater or lesser than 1.0.

5. Ventilation device according to claim 1, wherein the ventilation process is configured to be set by the control device such that
a) while supplying the fluid, a first volume that is present at the pressure $P_0$, and while discharging the fluid, a second volume that is present at the same pressure $P_0$, differs at most by 30% from the volume interval that is present in the pressure interval or
b) while supplying the fluid, a first pressure that is present at the volume $V_0$ and while discharging the fluid, a second pressure that is present at the same volume $V_0$, differs at most by 30% from the pressure interval that is present in the volume interval.

6. Ventilation device according to claim 1, wherein
a) the ventilation process is configured to be set over at least 60% of the pressure interval in such a way that while supplying the fluid, a first volume that is present at the pressure $P_0$, and while discharging the fluid, a second volume that is present at the same pressure $P_0$, differs at least by 1% from the volume interval that is present in the pressure interval or b) the ventilation process is configured to be set over at least 60% of the volume interval in such a way that while supplying the fluid, a first pressure that is present at the volume $V_0$, and while discharging the fluid, a second pressure that is present at the same volume $V_0$, differs at least by 1% from the pressure interval that is present in the volume interval.

7. Ventilation device according to claim 1, wherein the control device is configured to
   a) determine integrals of $f_{ZP}(P)$ and $f_{AP}(P)$ in the pressure interval and determine a difference between $\int f_{ZP}(P)\, dP$ and $\int f_{AP}(P)\, dP$ in the pressure interval or
   b) for determining integrals of $f_{ZV}(V)$ and $f_{AV}(V)$ in the volume interval and for determining a difference between $\int f_{ZV}(V)\, dV$ and $\int f_{AV}(V)\, dV$ in the volume interval.

8. Ventilation device according to claim 7, wherein the control device is configured to carry out multiple ventilation processes, in which the difference between
   a) $\int f_{ZP}(P)\, dP$ and $\int f_{AP}(P)\, dP$ in the pressure interval or
   b) $\int f_{ZV}(V)\, dV$ and $\int f_{AV}(V)\, dV$ in the volume interval is configured to be controlled, wherein a ratio of the difference to a critical difference that is established for a given patient is settable.

9. Method for operating a ventilation device provided for ventilating a patient, the ventilation device comprising:
   at least a fluid supply unit configured to supply a fluid into at least one airway;
   a fluid discharge unit configured to discharge the fluid from the at least one airway; and
   a control device, wherein the method comprises at least the following steps:
   a) carryout a ventilation process, including delivering at least a one-time supply of a fluid into the at least one airway and discharging at least a one-time discharge of the fluid from the airway by operating the ventilation device;
   wherein the ventilation process takes place within a pressure interval and within a volume interval;
   b) determining or setting a profile of at least one volume-pressure curve in a volume-pressure diagram by the control device during the ventilation process;
   wherein the curve has a first curve section $V=f_{ZP}(P)$ or $P=f_{ZV}(V)$, and a second curve section, $V=f_{AP}(P)$ or $P=f_{AV}(V)$, wherein the first curve section represents the profile of the supplied volume V and of the pressure P while supplying the fluid into the at least on airway, and the second curve section represents the profile of the discharged volume V and of the pressure P while discharging the fluid from the at least one airway wherein by use of the control device the ventilation process is configured to
   1) over at least 60% of the pressure interval, a ratio of an absolute value of a first slope of the first curve section at a pressure $P_0$, i.e. $df_{ZP}/d(P)(P_0)$, and an absolute value of a second slope of the second curve section, at the pressure $P_0$ has a value of at least 0.5 and at more 2.0, or
   2) over at least 60% of the volume interval, a ratio of an absolute value of a first slope of the first curve section at a volume $V_0$, i.e. $df_{AV}/d(V)(V_0)$, and an absolute value of a second slope of the second curve section, i.e., $df_{AV}/d(V)(V_0)$, at volume $V_0$ has a value of at least 0.5 and at most 2.0.

10. Method according to claim 9, wherein the control device determines the profile of the volume-pressure curve in the volume pressure diagram during the ventilation process for compliance of the airway according to one of $V=f_{CP}(P)$ or $P=f_{CV}(V)$; wherein the ventilation process in steps a) and b) is configured such that that over at least 60% of the pressure interval or over at least 60% of the volume interval, a ratio of
   each of $df_{AP}/d(P)\,(P_0)$, $df_{ZP}/d(P)\,(P_0)$ and
   an absolute value of a measure of the change in the first volume of the compliance that is present at a pressure $P_0$, i.e., $dfc/d(P)\,(P_0)$, or a ratio of
   each of $df_{AV}/d(V)\,(V_0)$, $df_{ZV}/d(V)\,(V_0)$ and
   an absolute value of a measure of the change in the first pressure of the compliance that is present at a volume $V_0$, i.e., $dfc/d(V)\,(V_0)$, has a value of at least 0.5 and at most 2.0.

11. Method according to claim 9, wherein the ventilation process is configured such that that over at least 60% of the pressure interval or 60% of the volume interval, the ratio has a value of at least 0.67 and at most 1.5.

12. Method according to claim 9, wherein in step b) or in a further step c) the control device carries out a determination or a setting of an area; wherein this area in the volume-pressure diagram is enclosed by the first curve section and the second curve section of the one ventilation process.

13. Method according to claim 12, wherein in the at least one ventilation process, a ratio of the area to a critical area that is established for a given patient is set.

14. Method according to claim 9, wherein the ventilation device includes a visualization apparatus, wherein at least one of the following parameters is visually discernibly displayed via the visualization apparatus:
   a) a measure for a size of the area; or
   b) a measure for a change in the area over multiple ventilation processes; or
   c) a measure for a ratio of the area to a critical area that is established for a given patient; or
   d) a measure for a change in the ratio of the area to a critical area that is established for a given patient over multiple ventilation processes.

* * * * *